US007976476B2

(12) United States Patent
Freeman et al.

(10) Patent No.: US 7,976,476 B2
(45) Date of Patent: Jul. 12, 2011

(54) DEVICE AND METHOD FOR VARIABLE SPEED LANCET

(75) Inventors: Dom Freeman, La Honda, CA (US); Dirk Boecker, Palo Alto, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 1107 days.

(21) Appl. No.: 11/687,031

(22) Filed: Mar. 16, 2007

(65) Prior Publication Data

US 2007/0260271 A1 Nov. 8, 2007

Related U.S. Application Data

(60) Division of application No. 10/420,535, filed on Apr. 21, 2003, now Pat. No. 7,258,693, which is a continuation-in-part of application No. 10/324,053, filed on Dec. 18, 2002, now Pat. No. 7,713,214, which is a continuation-in-part of application No. 10/127,395, filed on Apr. 19, 2002, now Pat. No. 7,025,774.

(60) Provisional application No. 60/374,304, filed on Apr. 19, 2002.

(51) Int. Cl.
*A61B 5/00* (2006.01)

(52) U.S. Cl. ........................................ 600/583; 606/181
(58) Field of Classification Search ................... 606/181, 606/182; 600/573, 583
See application file for complete search history.

(56) References Cited

U.S. PATENT DOCUMENTS

| 2,061 | A | 4/1841 | Osdel | 606/182 |
|---|---|---|---|---|
| 55,620 | A | 6/1866 | Capewell | 606/181 |
| 1,135,465 | A | 4/1915 | Pollock | 606/181 |
| 1,733,847 | A | 10/1929 | Wilmot | |
| 2,258,857 | A | 10/1941 | McCann | 601/81 |
| 2,628,319 | A | 2/1953 | Vang | 310/15 |
| 2,714,890 | A | 8/1955 | Alfred | 606/169 |
| 2,763,935 | A | 9/1956 | Whaley | 33/511 |
| 2,801,633 | A | 8/1957 | Mauze et al. | |
| 3,046,987 | A | 7/1962 | Ehrlich | 128/314 |
| 3,030,959 | A | 9/1962 | Grunert | 128/329 |
| 3,086,288 | A | 4/1963 | Balamuth | 30/277.4 |
| 3,208,452 | A | 9/1965 | Stern | 606/182 |
| 3,358,689 | A | 12/1967 | Higgins | 128/329 |
| 3,412,729 | A | 11/1968 | Smith, Jr. | 128/2.05 |
| 3,448,307 | A | 6/1969 | Rudolph | 310/23 |
| 3,494,358 | A | 2/1970 | Grossenbacher | 128/218 |
| 3,620,209 | A | 11/1971 | Kravitz | 601/79 |
| 3,626,929 | A | 12/1971 | Sanz | 128/2 R |

(Continued)

FOREIGN PATENT DOCUMENTS

DE 2206674 8/1972

(Continued)

*Primary Examiner* — Michael J Milano
*Assistant Examiner* — Victor X Nguyen
(74) *Attorney, Agent, or Firm* — Paul Davis; Goodwin Procter LLP

(57) ABSTRACT

A method of penetrating tissue is provided. The method uses a lancet driver to advance a lancet into the tissue; advancing the lancet at a first desired velocity in a first layer of tissue; advancing the lancet at a second desired velocity in a second layer of tissue; and advancing the lancet at a third desired velocity in a third layer of tissue. In one embodiment, the method may including using a processor having logic for controlling velocity of the lancet in each layer of tissue.

5 Claims, 5 Drawing Sheets

U.S. PATENT DOCUMENTS

| | | | |
|---|---|---|---|
| 3,628,026 A | 12/1971 | Cronin | 250/214.1 |
| 3,665,672 A | 5/1972 | Speelman | 53/435 |
| 3,673,475 A | 6/1972 | Britton | 318/122 |
| 3,712,293 A | 1/1973 | Mielke, Jr. | 128/2 |
| 3,734,812 A | 5/1973 | Yazawa | 428/107 |
| 3,742,954 A | 7/1973 | Strickland | 128/302 |
| 3,780,960 A | 12/1973 | Tokuno | 242/555.2 |
| 3,832,776 A | 9/1974 | Sawyer | 30/272 |
| 3,836,148 A | 9/1974 | Manning | 273/368 |
| 3,851,543 A | 12/1974 | Krom | 74/493 |
| 3,853,010 A | 12/1974 | Christen | 73/864.24 |
| 3,924,818 A | 12/1975 | Pfeifle | 242/364.7 |
| 3,938,526 A | 2/1976 | Anderson | 128/303.1 |
| 3,953,172 A | 4/1976 | Shapiro | 23/230 |
| 3,971,365 A | 7/1976 | Smith | 128/2.17 |
| 4,057,394 A | 11/1977 | Genshaw | 23/230 |
| 4,077,406 A | 3/1978 | Sandhage | 604/61 |
| 4,109,655 A | 8/1978 | Chaconac | 128/253 |
| 4,139,011 A | 2/1979 | Benoit | 606/182 |
| 4,154,228 A | 5/1979 | Feldstein | 606/169 |
| 4,168,130 A | 9/1979 | Barth | 404/99 |
| 4,184,486 A | 1/1980 | Papa | 600/373 |
| 4,190,420 A | 2/1980 | Covington | 422/63 |
| 4,191,193 A | 3/1980 | Seo | 600/488 |
| 4,193,690 A | 3/1980 | Levenson | 356/301 |
| 4,203,446 A | 5/1980 | Hofert | 606/182 |
| 4,207,870 A | 6/1980 | Eldridge | 128/766 |
| 4,223,674 A | 9/1980 | Fluent | 604/504 |
| 4,224,125 A | 9/1980 | Nakamura | 204/195 B |
| 4,224,949 A | 9/1980 | Scott | 128/734 |
| 4,230,118 A | 10/1980 | Holman et al. | 128/314 |
| 4,240,439 A | 12/1980 | Abe | 600/412 |
| 4,254,083 A | 3/1981 | Columbus | 422/55 |
| 4,258,001 A | 3/1981 | Pierce | 422/56 |
| 4,259,653 A | 3/1981 | McGonigal | 310/15 |
| 4,299,230 A | 11/1981 | Kubota | 600/300 |
| 4,301,412 A | 11/1981 | Hill | 324/442 |
| 4,321,397 A | 3/1982 | Nix | 548/366 |
| 4,338,174 A | 7/1982 | Tamura | 204/195 |
| 4,340,669 A | 7/1982 | Bauer | 435/14 |
| 4,350,762 A | 9/1982 | De Luca | 435/10 |
| 4,353,984 A | 10/1982 | Yamada | 435/14 |
| 4,356,826 A | 11/1982 | Kubota | 600/300 |
| 4,360,016 A | 11/1982 | Sarrine | 128/763 |
| 4,388,922 A | 6/1983 | Telang | 604/319 |
| 4,391,905 A | 7/1983 | Bauer | 435/14 |
| 4,391,906 A | 7/1983 | Bauer | 435/14 |
| 4,392,933 A | 7/1983 | Nakamura | 204/403.14 |
| 4,394,512 A | 7/1983 | Batz | 548/365 |
| 4,397,556 A | 8/1983 | Muller | 356/301 |
| 4,407,008 A | 9/1983 | Schmidt | 356/301 |
| 4,411,266 A | 10/1983 | Cosman | 128/303.18 |
| 4,414,975 A | 11/1983 | Ryder | 128/314 |
| 4,418,037 A | 11/1983 | Katsuyama | 422/56 |
| 4,420,564 A | 12/1983 | Tsuji | 435/288 |
| 4,425,039 A | 1/1984 | Grant | 356/35.5 |
| 4,426,451 A | 1/1984 | Columbus | 436/518 |
| 4,426,884 A | 1/1984 | Polchaninoff | 73/172 |
| 4,440,301 A | 4/1984 | Intengan | 206/456 |
| 4,442,836 A | 4/1984 | Meinecke | 128/314 |
| 4,442,972 A | 4/1984 | Sahay | 236/1 EA |
| 4,449,529 A | 5/1984 | Burns | 606/182 |
| 4,462,405 A | 7/1984 | Ehrlich | 606/182 |
| 4,469,110 A | 9/1984 | Slama | 128/770 |
| 4,517,978 A | 5/1985 | Levin | 128/314 |
| 4,518,384 A | 5/1985 | Tarello | 604/61 |
| 4,523,994 A | 6/1985 | Shono | 549/352 |
| 4,535,769 A | 8/1985 | Burns | 128/314 |
| 4,535,773 A | 8/1985 | Yoon | 606/185 |
| 4,537,197 A | 8/1985 | Hulka | 128/633 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,561,445 A | 12/1985 | Berke | 128/642 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,586,819 A | 5/1986 | Tochigi | 356/301 |
| 4,590,411 A | 5/1986 | Kelly | 318/687 |
| 4,595,479 A | 6/1986 | Kimura | 204/294 |
| 4,600,014 A | 7/1986 | Beraha | 128/754 |
| 4,603,209 A | 7/1986 | Tsien | 549/352 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia | 600/583 |
| 4,637,393 A | 1/1987 | Ray | 128/305 |
| 4,637,403 A | 1/1987 | Garcia | 600/583 |
| 4,643,189 A | 2/1987 | Mintz | 128/314 |
| 4,648,408 A | 3/1987 | Hutcheson | 128/770 |
| 4,648,714 A | 3/1987 | Benner | 356/301 |
| 4,653,511 A | 3/1987 | Goch | 128/763 |
| 4,653,513 A | 3/1987 | Dombrowski | 600/578 |
| 4,655,225 A | 4/1987 | Dahne | 600/316 |
| 4,661,768 A | 4/1987 | Carusillo | |
| 4,666,438 A | 5/1987 | Raulerson | 604/272 |
| 4,676,244 A | 6/1987 | Enstrom | 128/314 |
| 4,677,979 A | 7/1987 | Burns | 128/314 |
| 4,678,277 A | 7/1987 | Delhaye | 356/301 |
| 4,682,892 A | 7/1987 | Chawla | 356/353 |
| 4,702,594 A | 10/1987 | Grant | 356/35.5 |
| 4,711,245 A | 12/1987 | Higgins | 128/635 |
| 4,712,460 A | 12/1987 | Allen | 83/208 |
| 4,712,548 A | 12/1987 | Enstrom | 128/314 |
| 4,714,462 A | 12/1987 | DiDomenico | 604/67 |
| 4,715,374 A | 12/1987 | Maggio | 128/314 |
| 4,731,330 A | 3/1988 | Hill | 436/16 |
| 4,731,726 A | 3/1988 | Allen, III | 600/300 |
| 4,734,360 A | 3/1988 | Phillips | 435/25 |
| 4,735,203 A | 4/1988 | Ryder | 128/314 |
| 4,737,458 A | 4/1988 | Batz | 435/28 |
| 4,750,489 A | 6/1988 | Berkman | 606/166 |
| 4,753,776 A | 6/1988 | Hillman | 422/101 |
| 4,756,884 A | 7/1988 | Hillman | 422/73 |
| 4,757,022 A | 7/1988 | Shults et al. | 435/291 |
| 4,758,323 A | 7/1988 | Davis | 204/403 |
| 4,774,192 A | 9/1988 | Teriniello | 436/530 |
| 4,784,486 A | 11/1988 | Van Wagenen | 356/301 |
| 4,787,398 A | 11/1988 | Garcia | 600/583 |
| 4,790,979 A | 12/1988 | Teriniello | 422/56 |
| 4,794,926 A | 1/1989 | Munsch et al. | 606/183 |
| 4,797,283 A | 1/1989 | Allen | 424/443 |
| 4,814,142 A | 3/1989 | Gleisner | 422/56 |
| 4,814,661 A | 3/1989 | Ratzlaff | 310/328 |
| 4,817,603 A | 4/1989 | Turner | 606/182 |
| 4,818,493 A | 4/1989 | Coville | 422/102 |
| 4,820,010 A | 4/1989 | Sciefres | 385/43 |
| 4,820,399 A | 4/1989 | Senda | 204/403 |
| 4,823,806 A | 4/1989 | Bajada | 600/557 |
| 4,824,639 A | 4/1989 | Hildenbrand | 422/56 |
| RE32,922 E | 5/1989 | Levin et al. | 128/314 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeill | 435/53 |
| 4,836,904 A | 6/1989 | Armstrong | 204/294 |
| 4,840,893 A | 6/1989 | Hill | 435/6 |
| 4,844,095 A | 7/1989 | Chiodo | 128/314 |
| 4,845,392 A | 7/1989 | Mumbower | 310/14 |
| 4,850,973 A | 7/1989 | Jordan | 604/157 |
| 4,857,274 A | 8/1989 | Simon | 422/72 |
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |

| Patent No. | Kind | Date | Name | Class |
|---|---|---|---|---|
| 4,897,173 | A | 1/1990 | Nankai | 204/403 |
| 4,900,424 | A | 2/1990 | Birch | 204/409 |
| 4,900,666 | A | 2/1990 | Phillips | 435/25 |
| 4,911,794 | A | 3/1990 | Parce | 204/1 T |
| 4,920,977 | A | 5/1990 | Haynes | 128/770 |
| 4,924,879 | A | 5/1990 | O'Brien | |
| 4,935,346 | A | 6/1990 | Phillips | 435/14 |
| 4,938,218 | A | 7/1990 | Goodman | 128/633 |
| 4,940,468 | A | 7/1990 | Petillo | 606/170 |
| 4,944,304 | A | 7/1990 | Nishina | 128/667 |
| 4,945,045 | A | 7/1990 | Forrest | 435/25 |
| 4,946,795 | A | 8/1990 | Gibbons | 436/179 |
| 4,948,727 | A | 8/1990 | Cass | 435/18 |
| 4,948,961 | A | 8/1990 | Hillman | 250/252.1 |
| 4,952,373 | A | 8/1990 | Sugarman | 422/99 |
| 4,952,515 | A | 8/1990 | Gleisner | 436/169 |
| 4,953,552 | A | 9/1990 | DeMarzo | 128/635 |
| 4,953,976 | A | 9/1990 | Adler-Golden | 356/301 |
| 4,963,498 | A | 10/1990 | Hillman | 436/69 |
| 4,966,581 | A | 10/1990 | Landau | 604/72 |
| 4,966,646 | A | 10/1990 | Zdeblick | 156/633 |
| 4,966,671 | A | 10/1990 | Nylander | 204/153.14 |
| 4,975,581 | A | 12/1990 | Robinson | 250/339 |
| 4,976,724 | A | 12/1990 | Nieto | 606/182 |
| 4,977,910 | A | 12/1990 | Miyahara | 134/7 |
| 4,983,178 | A | 1/1991 | Schnell | 606/181 |
| 4,984,085 | A | 1/1991 | Landowski | 358/213 |
| 4,990,154 | A | 2/1991 | Brown | 606/182 |
| 4,995,402 | A | 2/1991 | Smith | 600/584 |
| 4,999,582 | A | 3/1991 | Parks | 324/438 |
| 5,001,054 | A | 3/1991 | Wagner | 435/14 |
| 5,001,873 | A | 3/1991 | Rufin | 451/39 |
| 5,004,923 | A | 4/1991 | Hillman | 250/341 |
| 5,010,772 | A | 4/1991 | Bourland | 73/862.04 |
| 5,010,774 | A | 4/1991 | Kikuo | 73/862.04 |
| 5,014,718 | A | 5/1991 | Mitchen | 128/771 |
| 5,019,974 | A | 5/1991 | Beckers | 364/413.02 |
| 5,026,388 | A | 6/1991 | Ingalz | 606/182 |
| D318,331 | S | 7/1991 | Phillips | D24/169 |
| 5,028,142 | A | 7/1991 | Ostoich et al. | 366/273 |
| 5,029,583 | A | 7/1991 | Meserol | 600/316 |
| 5,035,704 | A | 7/1991 | Lambert | 606/182 |
| 5,039,617 | A | 8/1991 | McDonald | 436/69 |
| 5,043,143 | A | 8/1991 | Shaw | 422/65 |
| 5,046,496 | A | 9/1991 | Betts | 600/352 |
| 5,047,044 | A | 9/1991 | Smith et al. | |
| 5,049,487 | A | 9/1991 | Phillips | 435/4 |
| 5,049,673 | A | 9/1991 | Tsien | 549/352 |
| 5,054,487 | A | 10/1991 | Clarke | 128/633 |
| 5,054,499 | A | 10/1991 | Swierczek | 128/770 |
| 5,057,082 | A | 10/1991 | Burchette, Jr. | 604/164 |
| 5,057,277 | A | 10/1991 | Mauze | 422/56 |
| 5,059,394 | A | 10/1991 | Phillips | 422/68.1 |
| 5,059,789 | A | 10/1991 | Salcudean | 435/4 |
| 5,060,174 | A | 10/1991 | Gross | 702/139 |
| 5,062,898 | A | 11/1991 | McDermott | 134/7 |
| 5,070,874 | A | 12/1991 | Barnes | 128/633 |
| 5,070,886 | A | 12/1991 | Mitchen | 128/771 |
| 5,074,872 | A | 12/1991 | Brown | 606/182 |
| 5,077,017 | A | 12/1991 | Gorin | 422/100 |
| 5,077,199 | A | 12/1991 | Basagni | 435/14 |
| 5,080,865 | A | 1/1992 | Leiner | 422/68.1 |
| 5,086,229 | A | 2/1992 | Rosenthal | 250/341 |
| 5,089,112 | A | 2/1992 | Skotheim | 204/403 |
| 5,092,842 | A | 3/1992 | Bechtold | 604/135 |
| 5,094,943 | A | 3/1992 | Siedel | 435/25 |
| 5,096,669 | A | 3/1992 | Lauks | 204/403.02 |
| 5,097,810 | A | 3/1992 | Fishman | 600/556 |
| 5,100,427 | A | 3/1992 | Crossman | 606/182 |
| 5,100,428 | A | 3/1992 | Mumford | 606/182 |
| 5,104,380 | A | 4/1992 | Holman | 604/117 |
| 5,104,619 | A | 4/1992 | Castro | 422/56 |
| 5,104,813 | A | 4/1992 | Besemer | 436/179 |
| 5,107,764 | A | 4/1992 | Gasparrini | 101/425 |
| 5,108,564 | A | 4/1992 | Szuminsky | 204/153.12 |
| 5,108,889 | A | 4/1992 | Smith et al. | |
| 5,116,759 | A | 5/1992 | Klainer | 435/288 |
| 5,120,420 | A | 6/1992 | Nankai | 204/403 |
| 5,122,244 | A | 6/1992 | Hoenes | 204/153 |
| 5,126,034 | A | 6/1992 | Carter | 204/403 |
| 5,128,015 | A | 7/1992 | Szuminsky | 204/403 |
| 5,128,171 | A | 7/1992 | Gleisner | 427/2 |
| 5,132,801 | A | 7/1992 | Yamano | 358/213 |
| 5,133,730 | A | 7/1992 | Biro | 606/182 |
| 5,135,719 | A | 8/1992 | Hillman | 422/101 |
| 5,139,685 | A | 8/1992 | Castro | 210/767 |
| 5,140,161 | A | 8/1992 | Hillman | 250/341 |
| 5,141,868 | A | 8/1992 | Shanks | 435/288 |
| 5,144,139 | A | 9/1992 | Hillman | 250/341 |
| 5,145,565 | A | 9/1992 | Kater | 600/341 |
| 5,146,091 | A | 9/1992 | Knudson | 250/341.6 |
| 5,152,296 | A | 10/1992 | Simons | 128/670 |
| 5,152,775 | A | 10/1992 | Ruppert | 606/182 |
| 5,153,671 | A | 10/1992 | Miles | 356/301 |
| 5,156,611 | A | 10/1992 | Haynes | 606/181 |
| 5,162,525 | A | 11/1992 | Masilamani | 549/352 |
| 5,163,442 | A | 11/1992 | Ono | 128/760 |
| 5,164,598 | A | 11/1992 | Hillman et al. | 250/341 |
| 5,167,619 | A | 12/1992 | Wuchinich | 604/22 |
| 5,170,364 | A | 12/1992 | Gross | 702/139 |
| 5,174,726 | A | 12/1992 | Findlay | 417/205 |
| D332,490 | S | 1/1993 | Brown | D24/146 |
| 5,178,142 | A | 1/1993 | Harjunmaa | 128/633 |
| 5,179,005 | A | 1/1993 | Phillips | 435/14 |
| 5,181,910 | A | 1/1993 | Scanlon | 604/67 |
| 5,181,914 | A | 1/1993 | Zook | 604/307 |
| 5,183,042 | A | 2/1993 | Harjunmaa | 128/633 |
| 5,185,256 | A | 2/1993 | Nankai | 435/174 |
| 5,187,100 | A | 2/1993 | Matzinger | 436/16 |
| 5,188,118 | A | 2/1993 | Terwilliger | 600/566 |
| 5,189,751 | A | 3/1993 | Giuliani | 15/22.1 |
| 5,192,415 | A | 3/1993 | Yoshioka | 204/403 |
| 5,194,391 | A | 3/1993 | Mauze | 436/166 |
| 5,196,025 | A | 3/1993 | Ranalletta | 606/182 |
| 5,201,324 | A | 4/1993 | Swierczek | 128/770 |
| 5,205,920 | A | 4/1993 | Oyama | 204/403 |
| 5,209,028 | A | 5/1993 | McDermott | 51/426 |
| 5,211,652 | A | 5/1993 | Derbyshire | 606/182 |
| 5,212,879 | A | 5/1993 | Biro | 29/437 |
| 5,215,587 | A | 6/1993 | McConnellogue | 118/699 |
| 5,216,597 | A | 6/1993 | Beckers | 364/413.02 |
| 5,217,480 | A | 6/1993 | Haber | 606/182 |
| 5,218,966 | A | 6/1993 | Yamasawa | 600/499 |
| 5,222,504 | A | 6/1993 | Solomon | 600/557 |
| 5,228,972 | A | 7/1993 | Osaka | 204/415 |
| 5,229,282 | A | 7/1993 | Yoshioka | 435/177 |
| 5,230,866 | A | 7/1993 | Shartle | 422/103 |
| 5,231,993 | A | 8/1993 | Haber | 128/770 |
| 5,241,969 | A | 9/1993 | Carson | 600/566 |
| 5,247,932 | A | 9/1993 | Chung | 128/633 |
| 5,249,583 | A | 10/1993 | Mallaby | 600/567 |
| 5,250,066 | A | 10/1993 | Lambert | 606/181 |
| 5,251,126 | A | 10/1993 | Kahn | 364/413.11 |
| 5,253,656 | A | 10/1993 | Rincoe | 128/782 |
| 5,256,998 | A | 10/1993 | Becker | 335/229 |
| 5,264,103 | A | 11/1993 | Yoshioka | 204/403 |
| 5,264,105 | A | 11/1993 | Gregg | 204/403 |
| 5,264,106 | A | 11/1993 | McAleer | 204/403 |
| 5,266,179 | A | 11/1993 | Nankai | 204/401 |
| 5,266,359 | A | 11/1993 | Spielvogel | 427/388.4 |
| D342,573 | S | 12/1993 | Cerola | D24/147 |
| 5,267,974 | A | 12/1993 | Lambert | 604/195 |
| 5,272,087 | A | 12/1993 | El Murr | 435/291 |
| 5,277,181 | A | 1/1994 | Mendelson | 128/633 |
| 5,279,294 | A | 1/1994 | Anderson | 600/322 |
| 5,279,791 | A | 1/1994 | Aldrich | 422/58 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollman | 435/288 |
| 5,294,261 | A | 3/1994 | McDermott | 134/7 |
| 5,296,378 | A | 3/1994 | Sakata | 436/63 |
| 5,300,779 | A | 4/1994 | Hillman | 250/341 |
| 5,304,192 | A | 4/1994 | Crouse | 606/181 |
| 5,304,193 | A | 4/1994 | Zhadanov | 606/182 |
| 5,304,347 | A | 4/1994 | Mann | 422/67 |
| 5,304,468 | A | 4/1994 | Phillips | 435/14 |
| 5,306,623 | A | 4/1994 | Kiser | 435/14 |

| Patent No. | Kind | Date | Name | Classification |
|---|---|---|---|---|
| 5,307,263 | A | 4/1994 | Brown | 600/301 |
| 5,312,590 | A | 5/1994 | Gunasingham | 422/56 |
| 5,314,441 | A | 5/1994 | Cusack | 606/182 |
| 5,314,442 | A | 5/1994 | Morita | 606/182 |
| 5,315,793 | A | 5/1994 | Peterson | 451/2 |
| 5,316,012 | A | 5/1994 | Siegal | 128/744 |
| 5,318,583 | A | 6/1994 | Rabenau | 606/182 |
| 5,318,584 | A | 6/1994 | Lange | 606/182 |
| 5,320,607 | A | 6/1994 | Ishibashi | 604/115 |
| 5,320,808 | A | 6/1994 | Holen | 422/64 |
| 5,324,302 | A | 6/1994 | Crouse | 606/181 |
| 5,324,303 | A | 6/1994 | Strong | 606/181 |
| 5,330,634 | A | 7/1994 | Wong | 205/777.5 |
| 5,332,479 | A | 7/1994 | Uenoyama | 204/153.12 |
| 5,341,206 | A | 8/1994 | Pittaro | 356/301 |
| 5,342,382 | A | 8/1994 | Brinkerhoff | 606/184 |
| 5,344,703 | A | 9/1994 | Kovar | 428/312.6 |
| 5,350,392 | A | 9/1994 | Purcell | 606/182 |
| 5,352,351 | A | 10/1994 | White | 204/406 |
| 5,354,287 | A | 10/1994 | Wacks | 604/232 |
| 5,354,447 | A | 10/1994 | Uenoyama | 204/403 |
| 5,356,420 | A | 10/1994 | Czernecki | 606/182 |
| 5,360,410 | A | 11/1994 | Wacks | 604/232 |
| 5,365,699 | A | 11/1994 | Armstrong | 451/7 |
| 5,366,469 | A | 11/1994 | Steg | 606/182 |
| 5,366,470 | A | 11/1994 | Ramel | 606/183 |
| 5,366,609 | A | 11/1994 | White | 204/403 |
| 5,368,047 | A | 11/1994 | Suzuki | 600/578 |
| 5,370,509 | A | 12/1994 | Golding | 417/423.1 |
| 5,371,687 | A | 12/1994 | Holmes | 364/514 |
| 5,372,135 | A | 12/1994 | Mendelson | 600/322 |
| 5,375,397 | A | 12/1994 | Ferrand | 54/66 |
| 5,378,628 | A | 1/1995 | Graetzel | 435/288 |
| 5,382,346 | A | 1/1995 | Uenoyama | 204/403 |
| 5,383,885 | A | 1/1995 | Bland | 606/182 |
| 5,389,534 | A | 2/1995 | Gentezkow | 435/180 |
| 5,390,450 | A | 2/1995 | Goenka | 451/39 |
| 5,393,903 | A | 2/1995 | Graetzel | 556/137 |
| 5,395,339 | A | 3/1995 | Talonn | 604/111 |
| 5,395,387 | A | 3/1995 | Burns | 606/181 |
| 5,397,334 | A | 3/1995 | Schenk | 606/182 |
| 5,401,376 | A | 3/1995 | Foos | 204/415 |
| 5,402,798 | A | 4/1995 | Swierczek | 128/770 |
| 5,405,283 | A | 4/1995 | Goenka | 451/39 |
| 5,405,510 | A | 4/1995 | Betts | 205/782 |
| 5,405,511 | A | 4/1995 | White | 204/153.1 |
| 5,407,545 | A | 4/1995 | Hirose | 204/153.12 |
| 5,407,554 | A | 4/1995 | Saurer | 204/403 |
| 5,407,818 | A | 4/1995 | Gentzekow | 435/180 |
| 5,409,583 | A | 4/1995 | Yoshioka | 204/153.12 |
| 5,409,664 | A | 4/1995 | Allen | |
| 5,410,059 | A | 4/1995 | Fraser | 546/10 |
| 5,415,169 | A | 5/1995 | Siczek | 600/427 |
| 5,418,142 | A | 5/1995 | Kiser | 435/14 |
| 5,423,847 | A | 6/1995 | Strong et al. | 606/182 |
| 5,424,545 | A | 6/1995 | Block | 350/343 |
| 5,426,032 | A | 6/1995 | Phillips | 435/14 |
| 5,436,161 | A | 7/1995 | Bergstrom | 435/291 |
| 5,437,999 | A | 8/1995 | Diebold | 435/288 |
| 5,438,271 | A | 8/1995 | White | 324/444 |
| 5,443,701 | A | 8/1995 | Willner | 204/153 |
| 5,445,920 | A | 8/1995 | Saito | 430/311 |
| D362,719 | S | 9/1995 | Kaplan | D24/147 |
| 5,453,360 | A | 9/1995 | Yu | 435/28 |
| 5,454,828 | A | 10/1995 | Schraga | 606/181 |
| 5,456,875 | A | 10/1995 | Lambert | 264/328.1 |
| 5,459,325 | A | 10/1995 | Hueton | 250/458.1 |
| 5,460,182 | A | 10/1995 | Goodman | 600/342 |
| 5,462,533 | A | 10/1995 | Daugherty | 604/164 |
| 5,464,418 | A | 11/1995 | Schraga | 606/182 |
| 5,465,722 | A | 11/1995 | Fort | 600/447 |
| 5,471,102 | A | 11/1995 | Becker | 310/50 |
| 5,472,427 | A | 12/1995 | Rammler | 604/164.01 |
| 5,474,084 | A | 12/1995 | Cunniff | 600/557 |
| 5,476,474 | A | 12/1995 | Davis | 606/182 |
| 5,480,387 | A | 1/1996 | Gabriel | 604/134 |
| 5,487,748 | A | 1/1996 | Marshall | 606/182 |
| D367,109 | S | 2/1996 | Ryner | D24/224 |
| 5,490,505 | A | 2/1996 | Diab | 600/323 |
| 5,496,274 | A | 3/1996 | Graves | 604/86 |
| 5,496,453 | A | 3/1996 | Uenoyama | 205/777.5 |
| 5,498,542 | A | 3/1996 | Corey | 435/283.1 |
| 5,501,836 | A | 3/1996 | Myerson | 42/57 |
| 5,501,893 | A | 3/1996 | Laermer | 428/161 |
| 5,507,288 | A | 4/1996 | Bocker | 128/633 |
| 5,507,629 | A | 4/1996 | Jarvik | 417/423.3 |
| 5,508,171 | A | 4/1996 | Walling | 205/777.5 |
| 5,509,410 | A | 4/1996 | Hill | 128/637 |
| 5,510,266 | A | 4/1996 | Bonner et al. | 436/43 |
| 5,512,159 | A | 4/1996 | Yoshioka | 204/403 |
| 5,514,152 | A | 5/1996 | Smith et al. | |
| 5,515,170 | A | 5/1996 | Matzinger | 356/423 |
| 5,518,006 | A | 5/1996 | Mawhirt | 128/770 |
| D371,198 | S | 6/1996 | Savage | D24/169 |
| 5,524,636 | A | 6/1996 | Sarvazyan | 128/774 |
| 5,525,511 | A | 6/1996 | D'Costa | 435/287.9 |
| 5,525,518 | A | 6/1996 | Lundsgaard | 436/68 |
| 5,526,120 | A | 6/1996 | Jina | 356/446 |
| 5,527,333 | A | 6/1996 | Nikkels | 606/182 |
| 5,527,334 | A | 6/1996 | Kanner | 606/182 |
| 5,529,074 | A | 6/1996 | Greenfield | 600/557 |
| 5,540,676 | A | 7/1996 | Freiberg | |
| 5,540,709 | A | 7/1996 | Ramel | 606/183 |
| 5,543,326 | A | 8/1996 | Heller | 435/287.9 |
| 5,545,174 | A | 8/1996 | Schenk | 606/182 |
| 5,545,291 | A | 8/1996 | Smith | 438/107 |
| 5,547,702 | A | 8/1996 | Gleisner | 427/2.13 |
| D373,419 | S | 9/1996 | Muramatsu | D24/165 |
| 5,554,153 | A | 9/1996 | Costello | 606/9 |
| 5,554,166 | A | 9/1996 | Lange | 606/182 |
| 5,558,834 | A | 9/1996 | Chu | 422/55 |
| 5,562,384 | A | 10/1996 | Alvite | 414/226.01 |
| 5,562,696 | A | 10/1996 | Nobles | 606/185 |
| 5,563,031 | A | 10/1996 | Yu | 435/4 |
| 5,563,042 | A | 10/1996 | Phillips | 435/14 |
| 5,569,286 | A | 10/1996 | Peckham | 606/181 |
| 5,569,287 | A | 10/1996 | Tezuka | 606/182 |
| 5,571,132 | A | 11/1996 | Mawhirt | 606/182 |
| 5,575,284 | A | 11/1996 | Athan | 600/323 |
| 5,575,403 | A | 11/1996 | Charlton | 221/31 |
| 5,575,895 | A | 11/1996 | Ikeda | 204/403 |
| 5,582,697 | A | 12/1996 | Ikeda | 204/403 |
| 5,584,846 | A | 12/1996 | Mawhirt | 606/181 |
| 5,591,139 | A | 1/1997 | Lin | 604/264 |
| 5,593,852 | A | 1/1997 | Heller | 435/14 |
| 5,599,501 | A | 2/1997 | Carey | 422/64 |
| 5,605,837 | A | 2/1997 | Karimi | 436/14 |
| D378,612 | S | 3/1997 | Clark | D24/169 |
| 5,608,006 | A | 3/1997 | Myerson | 525/54.1 |
| 5,609,749 | A | 3/1997 | Yamauchi | 205/777.5 |
| 5,611,809 | A | 3/1997 | Marshall | 606/181 |
| 5,611,810 | A | 3/1997 | Arnold | 606/185 |
| 5,613,978 | A | 3/1997 | Harding | 606/181 |
| 5,616,135 | A | 4/1997 | Thorne | 604/192 |
| 5,617,851 | A | 4/1997 | Lipkovker | 600/573 |
| 5,618,297 | A | 4/1997 | Hart | 606/185 |
| 5,620,579 | A | 4/1997 | Genshaw | 204/402 |
| 5,620,863 | A | 4/1997 | Tomasco | 435/14 |
| 5,624,458 | A | 4/1997 | Lipscher | 606/181 |
| 5,624,459 | A | 4/1997 | Kortenbach | 606/185 |
| 5,624,537 | A | 4/1997 | Turner | 204/403 |
| D379,516 | S | 5/1997 | Rutter | D24/146 |
| 5,628,764 | A | 5/1997 | Schraga | 606/182 |
| 5,628,765 | A | 5/1997 | Morita | 606/182 |
| 5,628,890 | A | 5/1997 | Carter | 204/403 |
| 5,628,961 | A | 5/1997 | Davis | 422/63 |
| 5,630,828 | A | 5/1997 | Mawhirt | 606/187 |
| 5,630,986 | A | 5/1997 | Charlton | 422/64 |
| 5,632,410 | A | 5/1997 | Moulton | 221/79 |
| 5,640,954 | A | 6/1997 | Pfeiffer | 128/635 |
| D381,591 | S | 7/1997 | Rice | D10/81 |
| 5,643,306 | A | 7/1997 | Schraga | 606/182 |
| 5,643,308 | A | 7/1997 | Markman | 606/187 |
| 5,645,555 | A | 7/1997 | Davis | 606/182 |
| 5,647,851 | A | 7/1997 | Pokras | 604/131 |
| 5,650,062 | A | 7/1997 | Ikeda | 205/778 |
| 5,653,863 | A | 8/1997 | Genshaw | 205/777.5 |
| 5,657,760 | A | 8/1997 | Ying et al. | 128/660.03 |

| Patent No. | Date | Name | Class |
|---|---|---|---|
| 5,658,444 A | 8/1997 | Black | 204/415 |
| 5,660,791 A | 8/1997 | Brenneman | 422/58 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,676,143 A | 10/1997 | Simonsen | 128/633 |
| 5,678,306 A | 10/1997 | Bozeman | 29/888.025 |
| 5,680,858 A | 10/1997 | Hansen et al. | 128/635 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/504 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 33/3 R |
| 5,730,753 A | 3/1998 | Morita | 606/182 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A | 4/1998 | Lee | 606/189 |
| 5,736,103 A | 4/1998 | Pugh | 422/68.1 |
| 5,738,244 A | 4/1998 | Charlton et al. | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,746,898 A | 5/1998 | Preidel | 204/403 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Morita | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons et al. | |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,822,715 A | 10/1998 | Worthington | 702/19 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,828,943 A | 10/1998 | Brown | 434/258 |
| 5,829,589 A | 11/1998 | Nguyen | 206/366 |
| 5,830,219 A | 11/1998 | Bird | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,853,373 A | 12/1998 | Griffith | 600/554 |
| 5,854,074 A | 12/1998 | Charlton | 436/46 |
| D403,975 S | 1/1999 | Douglas | D10/81 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,858,804 A | 1/1999 | Zanzucchi | 506/9 |
| 5,860,922 A | 1/1999 | Gordon et al. | 600/431 |
| 5,863,800 A | 1/1999 | Eikmeier | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons et al. | |
| 5,872,713 A | 2/1999 | Douglas | 702/85 |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon | 600/583 |
| 5,879,373 A | 3/1999 | Roeper | 606/344 |
| 5,880,829 A | 3/1999 | Kauhaniemi | 356/246 |
| 5,882,494 A | 3/1999 | van Antwerp | 204/403 |
| 5,885,211 A | 3/1999 | Eppstein | 600/309 |
| 5,886,056 A | 3/1999 | Hershkowitz | 518/703 |
| 5,887,133 A | 3/1999 | Brown | 395/200.3 |
| 5,890,128 A | 3/1999 | Diaz | 705/2 |
| RE36,191 E | 4/1999 | Solomon | 395/308 |
| 5,891,053 A | 4/1999 | Sesekura | 600/583 |
| 5,893,848 A | 4/1999 | Negus | 606/41 |
| 5,893,870 A | 4/1999 | Talen | 606/201 |
| 5,897,493 A | 4/1999 | Brown | 600/300 |
| 5,897,569 A | 4/1999 | Kellogg | 606/169 |
| 5,899,855 A | 5/1999 | Brown | 600/301 |
| 5,899,915 A | 5/1999 | Saadat et al. | |
| 5,900,130 A | 5/1999 | Benvegnu | 204/453 |
| 5,902,731 A | 5/1999 | Ouyang | 435/26 |
| 5,906,921 A | 5/1999 | Ikeda | 435/25 |
| D411,619 S | 6/1999 | Duchon | D24/146 |
| 5,908,416 A | 6/1999 | Costello | 606/9 |
| 5,911,937 A | 6/1999 | Hekal | 264/255 |
| 5,912,134 A | 6/1999 | Shartle | 435/7.24 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,919,711 A | 7/1999 | Boyd | 436/178 |
| 5,921,963 A | 7/1999 | Erez | 604/192 |
| 5,922,188 A | 7/1999 | Ikeda | 204/777.5 |
| 5,922,530 A | 7/1999 | Yu | 435/4 |
| 5,922,591 A | 7/1999 | Anderson | 435/287.2 |
| RE36,268 E | 8/1999 | Szuminsky | 205/777.5 |
| 5,931,794 A | 8/1999 | Pitesky | 600/556 |
| 5,933,136 A | 8/1999 | Brown | 345/327 |
| 5,935,075 A | 8/1999 | Casscells et al. | 600/474 |
| 5,938,679 A | 8/1999 | Freeman | 606/181 |

| Patent No. | Date | Name | Class |
|---|---|---|---|
| 5,940,153 A | 8/1999 | Castaneda | |
| 5,942,102 A | 8/1999 | Hodges | 205/775 |
| 5,942,189 A | 8/1999 | Wolfbeis | 422/82.08 |
| 5,947,957 A | 9/1999 | Morris | 606/13 |
| 5,951,300 A | 9/1999 | Brown | 434/236 |
| 5,951,492 A | 9/1999 | Douglas | 600/583 |
| 5,951,493 A | 9/1999 | Douglas et al. | 600/583 |
| 5,951,582 A | 9/1999 | Thorne | 606/182 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,957,846 A | 9/1999 | Chiang | 600/447 |
| 5,958,199 A | 9/1999 | Miyamoto | 204/403 |
| 5,959,098 A | 9/1999 | Goldberg | 536/25.3 |
| 5,960,403 A | 9/1999 | Brown | 705/2 |
| 5,961,451 A | 10/1999 | Reber | 600/322 |
| 5,964,718 A | 10/1999 | Duchon | 600/583 |
| 5,965,380 A | 10/1999 | Heller | 435/14 |
| 5,968,063 A | 10/1999 | Chu | 606/185 |
| 5,968,760 A | 10/1999 | Phillips | 435/14 |
| 5,968,836 A | 10/1999 | Matzinger | 436/169 |
| 5,971,941 A | 10/1999 | Simons | 606/573 |
| 5,972,199 A | 10/1999 | Heller | 205/777.5 |
| 5,972,294 A | 10/1999 | Smith | 422/58 |
| 5,972,715 A | 10/1999 | Celentano | 436/164 |
| 5,974,124 A | 10/1999 | Schlueter | 379/106.02 |
| 5,976,085 A | 11/1999 | Kimball | 600/309 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,986,754 A | 11/1999 | Harding | 356/246 |
| 5,993,400 A | 11/1999 | Rincoe | 600/595 |
| 5,993,434 A | 11/1999 | Dev | 604/501 |
| D417,504 S | 12/1999 | Love | D24/169 |
| 5,997,476 A | 12/1999 | Brown | 600/300 |
| 5,997,561 A | 12/1999 | Boecker | 606/182 |
| 5,997,817 A | 12/1999 | Crismore | 422/58 |
| 5,997,818 A | 12/1999 | Hackner | 422/681 |
| 6,001,067 A | 12/1999 | Shults | 600/584 |
| 6,007,497 A | 12/1999 | Huitema | 600/567 |
| D418,602 S | 1/2000 | Prokop | D24/169 |
| 6,014,577 A | 1/2000 | Henning | 600/345 |
| 6,015,392 A | 1/2000 | Douglas | 600/583 |
| 6,018,289 A | 1/2000 | Sekura | 340/309.4 |
| 6,020,110 A | 2/2000 | Williams | 430/315 |
| 6,022,324 A | 2/2000 | Skinner | 600/566 |
| 6,022,366 A | 2/2000 | Schraga | 606/1.81 |
| 6,022,748 A | 2/2000 | Charych | 436/527 |
| 6,023,629 A | 2/2000 | Tamada | 600/347 |
| 6,023,686 A | 2/2000 | Brown | 705/37 |
| 6,027,459 A | 2/2000 | Shain et al. | |
| 6,030,399 A | 2/2000 | Ignotz | 606/167 |
| 6,030,827 A | 2/2000 | Davis | 435/287 |
| 6,030,967 A | 2/2000 | Marui | 514/215 |
| 6,032,059 A | 2/2000 | Henning | 600/345 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons | 422/100 |
| 6,037,178 A | 3/2000 | Leiner | 436/50 |
| 6,041,253 A | 3/2000 | Kost | 604/20 |
| 6,045,567 A | 4/2000 | Taylor | 606/167 |
| 6,046,055 A | 4/2000 | Wolfbeis | 436/172 |
| 6,048,352 A | 4/2000 | Douglas | 606/181 |
| D424,696 S | 5/2000 | Ray | D24/169 |
| 6,056,701 A | 5/2000 | Duchon | 600/583 |
| 6,059,815 A | 5/2000 | Lee | 606/209 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,243 A | 5/2000 | Anderson | 422/82.01 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,070,761 A | 6/2000 | Bloom | 222/81 |
| 6,071,249 A | 6/2000 | Cunningham | 600/578 |
| 6,071,250 A | 6/2000 | Douglas | 600/583 |
| 6,071,251 A | 6/2000 | Cunningham et al. | |
| 6,071,294 A | 6/2000 | Simons | 606/181 |
| 6,071,391 A | 6/2000 | Gotoh | 204/403 |
| 6,074,360 A | 6/2000 | Haar et al. | 604/57 |
| 6,077,408 A | 6/2000 | Miyamoto | 204/403 |
| 6,080,106 A | 6/2000 | Lloyd | 600/300 |
| 6,080,172 A | 6/2000 | Fujiwara | 606/166 |
| D428,150 S | 7/2000 | Ruf | D24/146 |
| 6,083,196 A | 7/2000 | Trautman | 604/46 |
| 6,083,710 A | 7/2000 | Heller | 435/14 |
| 6,084,660 A | 7/2000 | Shartle | 356/39 |
| 6,085,576 A | 7/2000 | Sunshine | 73/29.01 |
| 6,086,544 A | 7/2000 | Hibner | 600/568 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,091,975 A | 7/2000 | Daddona | 600/345 |
| 6,093,146 A | 7/2000 | Filangeri | 600/300 |
| 6,093,156 A | 7/2000 | Cunningham et al. | 600/573 |
| D428,993 S | 8/2000 | Lubs | D24/165 |
| 6,099,484 A | 8/2000 | Douglas | 600/583 |
| 6,099,802 A | 8/2000 | Pugh | 422/58 |
| 6,100,107 A | 8/2000 | Lei | 438/50 |
| 6,101,478 A | 8/2000 | Brown | 705/2 |
| 6,102,933 A | 8/2000 | Lee | 606/209 |
| 6,103,033 A | 8/2000 | Say | 156/73.1 |
| 6,103,509 A | 8/2000 | Sode | 435/190 |
| 6,104,940 A | 8/2000 | Watanabe | 600/345 |
| 6,106,751 A | 8/2000 | Talbot | 264/81 |
| 6,107,083 A | 8/2000 | Collins | 435/288 |
| 6,113,578 A | 9/2000 | Brown | 604/207 |
| 6,117,630 A | 9/2000 | Reber | 435/4 |
| 6,118,126 A | 9/2000 | Zanzucchi | 250/458.1 |
| 6,119,033 A | 9/2000 | Spigelman | 600/426 |
| 6,120,462 A | 9/2000 | Hibner | 600/566 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,126,804 A | 10/2000 | Andresen | 204/601 |
| 6,126,899 A | 10/2000 | Woudenberg | 422/50 |
| 6,129,823 A | 10/2000 | Hughes | 204/403.01 |
| 6,132,449 A | 10/2000 | Lum | 606/181 |
| 6,133,837 A | 10/2000 | Riley | 340/573.1 |
| 6,134,461 A | 10/2000 | Say | 600/345 |
| 6,136,013 A | 10/2000 | Marshall | 606/167 |
| 6,139,562 A | 10/2000 | Mauze | 606/171 |
| 6,143,164 A | 11/2000 | Heller | 600/583 |
| 6,144,837 A | 11/2000 | Quy | 434/307 R |
| 6,149,203 A | 11/2000 | Hanlon | 283/72 |
| 6,151,586 A | 11/2000 | Brown | 705/14 |
| 6,152,875 A | 11/2000 | Hakamata | 600/319 |
| 6,152,942 A | 11/2000 | Brenneman | 606/181 |
| 6,153,069 A | 11/2000 | Pottgen | 204/403 |
| RE36,991 E | 12/2000 | Yamamoto | 204/403 |
| 6,155,267 A | 12/2000 | Nelson | 128/899 |
| 6,155,992 A | 12/2000 | Henning et al. | 600/583 |
| 6,156,051 A | 12/2000 | Schraga | 606/181 |
| 6,157,442 A | 12/2000 | Raskas | 356/39 |
| 6,159,147 A | 12/2000 | Lichter | 600/300 |
| 6,159,424 A | 12/2000 | Kauhaniemi | 422/63 |
| 6,161,095 A | 12/2000 | Brown | 705/2 |
| 6,162,397 A | 12/2000 | Jurik | 422/56 |
| 6,162,611 A | 12/2000 | Heller | 435/14 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,168,957 B1 | 1/2001 | Matzinger | 436/518 |
| 6,171,325 B1 | 1/2001 | Mauze et al. | 606/171 |
| 6,172,743 B1 | 1/2001 | Kley et al. | 356/39 |
| 6,175,752 B1 | 1/2001 | Say | 600/345 |
| 6,176,847 B1 | 1/2001 | Humphreys | 604/246 |
| 6,176,865 B1 | 1/2001 | Mauze | 606/171 |
| 6,177,000 B1 | 1/2001 | Peterson | 205/777.5 |
| 6,177,931 B1 | 1/2001 | Alexander et al. | |
| 6,183,489 B1 | 2/2001 | Douglas | 606/181 |
| 6,186,145 B1 | 2/2001 | Brown | 128/897 |
| 6,190,612 B1 | 2/2001 | Berger | 422/82.07 |
| 6,191,852 B1 | 2/2001 | Paffhausen | 356/244 |
| 6,192,891 B1 | 2/2001 | Gravel | 128/920 |

| Patent | Date | Name | Class |
|---|---|---|---|
| 6,193,673 B1 | 2/2001 | Viola | 600/568 |
| 6,193,873 B1 | 2/2001 | Ohara | 205/792 |
| 6,194,900 B1 | 2/2001 | Freeman | 324/321 |
| 6,197,040 B1 | 3/2001 | LeVaughn | 606/182 |
| 6,197,257 B1 | 3/2001 | Raskas | 422/82.05 |
| 6,200,773 B1 | 3/2001 | Ouyang | 435/26 |
| 6,203,504 B1 | 3/2001 | Latterell | 600/576 |
| 6,206,841 B1 | 3/2001 | Cunningham et al. | 600/584 |
| 6,210,133 B1 | 4/2001 | Aboul-Hosn | 417/423.1 |
| 6,210,272 B1 | 4/2001 | Brown | 463/1 |
| 6,210,369 B1 | 4/2001 | Wilmot | 604/157 |
| 6,210,420 B1 | 4/2001 | Mauze | 606/182 |
| 6,210,421 B1 | 4/2001 | Bocker | 606/182 |
| 6,212,417 B1 | 4/2001 | Ikeda | 204/403.14 |
| 6,214,626 B1 | 4/2001 | Meller | 436/165 |
| 6,214,804 B1 | 4/2001 | Felgner | 514/44 |
| 6,218,571 B1 | 4/2001 | Zheng | 562/61 |
| 6,219,574 B1 | 4/2001 | Cormier | 604/20 |
| 6,221,023 B1 | 4/2001 | Matsuba | 600/486 |
| 6,221,238 B1 | 4/2001 | Grundig | 205/777.5 |
| 6,225,078 B1 | 5/2001 | Ikeda | 435/25 |
| 6,228,100 B1 | 5/2001 | Schraga | |
| 6,230,051 B1 | 5/2001 | Cormier | 604/20 |
| 6,230,501 B1 | 5/2001 | Bailey | 62/51.1 |
| 6,231,531 B1 | 5/2001 | Lum | 601/46 |
| 6,233,471 B1 | 5/2001 | Berner | 600/345 |
| 6,233,539 B1 | 5/2001 | Brown | 703/11 |
| 6,234,772 B1 | 5/2001 | Wampler | 417/423.12 |
| 6,240,393 B1 | 5/2001 | Brown | 705/1 |
| D444,235 S | 6/2001 | Roberts | D24/169 |
| 6,241,862 B1 | 6/2001 | McAleer | 204/403 |
| 6,242,207 B1 | 6/2001 | Douglas | 435/25 |
| 6,245,060 B1 | 6/2001 | Loomis | 606/9 |
| 6,245,215 B1 | 6/2001 | Douglas | 205/775 |
| 6,246,992 B1 | 6/2001 | Brown | 705/2 |
| 6,248,065 B1 | 6/2001 | Brown | 600/300 |
| 6,251,083 B1 | 6/2001 | Yum | 600/584 |
| 6,251,121 B1 | 6/2001 | Saadat | 606/180 |
| 6,251,260 B1 | 6/2001 | Heller | 205/777.5 |
| 6,251,344 B1 | 6/2001 | Goldstein | 422/123 |
| D444,557 S | 7/2001 | Levaughn | D24/146 |
| 6,254,831 B1 | 7/2001 | Barnard | 422/82.08 |
| 6,256,533 B1 | 7/2001 | Vuzhakov | 604/21 |
| 6,258,111 B1 | 7/2001 | Ross. | 606/171 |
| 6,258,229 B1 | 7/2001 | Winarta | 204/403 |
| 6,258,254 B1 | 7/2001 | Miyamoto | 205/777.5 |
| 6,261,241 B1 | 7/2001 | Burbank | 600/564 |
| 6,261,245 B1 | 7/2001 | Kawai | 600/576 |
| 6,261,519 B1 | 7/2001 | Harding | |
| 6,264,635 B1 | 7/2001 | Wampler | 604/151 |
| 6,268,161 B1 | 7/2001 | Han | 435/14 |
| 6,268,162 B1 | 7/2001 | Phillips | 435/14 |
| 6,269,314 B1 | 7/2001 | Iitawaki | 702/23 |
| 6,270,455 B1 | 8/2001 | Brown | 600/300 |
| 6,270,637 B1 | 8/2001 | Crismore | 204/403 |
| 6,272,359 B1 | 8/2001 | Kivela | 455/567 |
| 6,272,364 B1 | 8/2001 | Kurnik | 600/345 |
| 6,275,717 B1 | 8/2001 | Gross | 600/345 |
| 6,280,254 B1 | 8/2001 | Wu | 439/630 |
| 6,281,006 B1 | 8/2001 | Heller | 435/287.9 |
| 6,283,926 B1 | 9/2001 | Cunningham | 600/573 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |
| 6,285,454 B1 | 9/2001 | Douglas | 356/446 |
| 6,289,254 B1 | 9/2001 | Shimizu | 700/96 |
| 6,290,683 B1 | 9/2001 | Erez | 604/273 |
| 6,294,897 B1 | 9/2001 | Champlin | 320/153 |
| 6,295,506 B1 | 9/2001 | Heinonen | 702/104 |
| 6,299,578 B1 | 10/2001 | Kurnik | 600/309 |
| 6,299,596 B1 | 10/2001 | Ding | 604/96.01 |
| 6,299,757 B1 | 10/2001 | Feldman | 205/775 |
| 6,302,844 B1 | 10/2001 | Walker | 600/300 |
| 6,302,855 B1 | 10/2001 | Lav | 600/584 |
| 6,305,804 B1 | 10/2001 | Rice | 351/221 |
| 6,306,104 B1 | 10/2001 | Cunningham | 600/573 |
| 6,306,152 B1 | 10/2001 | Verdonk | 606/182 |
| 6,306,347 B1 | 10/2001 | Mason | 422/58 |
| 6,309,351 B1 | 10/2001 | Kurnik | 600/309 |
| 6,309,535 B1 | 10/2001 | Williams | 205/777.5 |
| 6,312,612 B1 | 11/2001 | Sherman | 216/2 |
| 6,315,738 B1 | 11/2001 | Nishikawa | |
| 6,318,970 B1 | 11/2001 | Backhouse | 417/92 |
| 6,319,210 B1 | 11/2001 | Douglas | 600/583 |
| 6,322,574 B1 | 11/2001 | Lloyd | 606/181 |
| 6,322,808 B1 | 11/2001 | Trautman | 424/448 |
| 6,322,963 B1 | 11/2001 | Bauer | 435/4 |
| 6,329,161 B1 | 12/2001 | Heller | 435/14 |
| 6,330,426 B2 | 12/2001 | Brown | 434/307 R |
| 6,331,163 B1 | 12/2001 | Kaplan | 600/486 |
| 6,332,871 B1 | 12/2001 | Douglas | 600/583 |
| 6,334,363 B1 | 1/2002 | Testud | 73/862 |
| 6,334,778 B1 | 1/2002 | Brown | 434/258 |
| 6,334,856 B1 | 1/2002 | Allen | 604/191 |
| 6,335,203 B1 | 1/2002 | Patel | 436/169 |
| 6,336,900 B1 | 1/2002 | Alleckson | 600/485 |
| 6,338,790 B1 | 1/2002 | Feldman | 205/777.5 |
| 6,346,120 B1 | 2/2002 | Yamazaki | 623/3.13 |
| 6,349,229 B1 | 2/2002 | Watanabe | 600/345 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas | 600/583 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,364,890 B1 | 4/2002 | Lum | 606/181 |
| 6,368,273 B1 | 4/2002 | Brown | 600/300 |
| 6,375,469 B1 | 4/2002 | Brown | 434/236 |
| 6,375,627 B1 | 4/2002 | Mauze | 600/584 |
| 6,379,301 B1 | 4/2002 | Worthington | 600/309 |
| 6,379,317 B1 | 4/2002 | Kintzig | 600/573 |
| 6,379,324 B1 | 4/2002 | Gartstein | 604/22 |
| 6,379,969 B1 | 4/2002 | Mauze et al. | |
| 6,381,577 B1 | 4/2002 | Brown | 705/2 |
| D456,910 S | 5/2002 | Clark | D24/225 |
| 6,387,709 B1 | 5/2002 | Mason | 436/164 |
| 6,391,005 B1 | 5/2002 | Lum | 604/117 |
| 6,395,227 B1 | 5/2002 | Kiser | 422/56 |
| 6,398,522 B2 | 6/2002 | Skill | 417/410.3 |
| 6,398,562 B1 | 6/2002 | Butler | 439/91 |
| 6,399,394 B1 | 6/2002 | Dahm | 436/180 |
| 6,402,701 B1 | 6/2002 | Kaplan | 600/567 |
| 6,402,704 B1 | 6/2002 | McMorrow | 600/576 |
| 6,409,740 B1 | 6/2002 | Kuhr | 606/182 |
| 6,413,410 B1 | 7/2002 | Hodges | 205/775 |
| 6,413,411 B1 | 7/2002 | Pottgen | 205/777.5 |
| 6,415,821 B2 | 7/2002 | Kamholz | 137/827 |
| 6,420,128 B1 | 7/2002 | Ouyang | 435/14 |
| 6,421,633 B1 | 7/2002 | Heinonen | 703/11 |
| 6,423,014 B1 | 7/2002 | Churchill et al. | |
| 6,428,664 B1 | 8/2002 | Bhullar | 204/403.03 |
| 6,436,055 B1 | 8/2002 | Roe | 600/584 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,444,115 B1 | 9/2002 | Hodges | 205/792 |
| 6,447,265 B1 | 9/2002 | Antaki | 417/354 |
| 6,451,040 B1 | 9/2002 | Purcell | 606/1.81 |
| 6,453,810 B1 | 9/2002 | Rossmeisl | 101/123 |
| 6,458,258 B2 | 10/2002 | Taniike | 204/403 |
| 6,461,496 B1 | 10/2002 | Feldman | 205/777.5 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,472,220 B1 | 10/2002 | Simons | 436/63 |
| 6,475,360 B1 | 11/2002 | Hodges | 204/403.14 |
| 6,475,372 B1 | 11/2002 | Ohara | 205/777.5 |
| 6,475,436 B1 | 11/2002 | Schabbach | 422/64 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,488,827 B1 | 12/2002 | Shartle | 204/403 |
| 6,488,891 B2 | 12/2002 | Mason | 422/58 |
| 6,489,133 B2 | 12/2002 | Phillips | 435/14 |
| 6,491,709 B2 | 12/2002 | Sharma | 606/181 |

| Patent | Kind | Date | Inventor | Class |
|---|---|---|---|---|
| 6,491,870 | B2 | 12/2002 | Patel | 422/58 |
| 6,494,830 | B1 | 12/2002 | Wessel | 600/300 |
| 6,497,845 | B1 | 12/2002 | Sacherer | 422/104 |
| 6,501,404 | B2 | 12/2002 | Walker | 341/143 |
| 6,501,976 | B1 | 12/2002 | Sohrab | 600/347 |
| 6,503,209 | B2 | 1/2003 | Hakky et al. | |
| 6,503,210 | B1 | 1/2003 | Hirao | 600/576 |
| 6,503,231 | B1 | 1/2003 | Prausnitz | 604/272 |
| 6,503,290 | B1 | 1/2003 | Jarosinski et al. | 75/252 |
| 6,503,381 | B1 | 1/2003 | Gotoh | 204/403.14 |
| 6,506,165 | B1 | 1/2003 | Sweeney | 600/562 |
| 6,506,168 | B1 | 1/2003 | Fathallah | 600/578 |
| 6,506,575 | B1 | 1/2003 | Knappe | 435/25 |
| 6,508,785 | B1 | 1/2003 | Eppstein | 604/113 |
| 6,512,986 | B1 | 1/2003 | Harmon | 702/84 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor | 206/305 |
| 6,521,110 | B1 | 2/2003 | Hodges | 204/403.14 |
| 6,521,182 | B1 | 2/2003 | Shartle | 422/58 |
| 6,527,521 | B2 | 3/2003 | Noda | 417/355 |
| 6,527,716 | B1 | 3/2003 | Eppstein | 600/309 |
| 6,527,778 | B2 | 3/2003 | Athanasiou | 606/80 |
| 6,529,377 | B1 | 3/2003 | Nelson | 361/699 |
| 6,530,892 | B1 | 3/2003 | Kelly | 600/583 |
| 6,530,937 | B1 | 3/2003 | Schraga | 606/182 |
| 6,531,322 | B1 | 3/2003 | Jurik | 436/95 |
| 6,533,949 | B1 | 3/2003 | Yeshurun | 216/11 |
| 6,537,207 | B1 | 3/2003 | Rice | 600/127 |
| 6,537,242 | B1 | 3/2003 | Palmer | 604/22 |
| 6,537,292 | B1 | 3/2003 | Lee | 606/182 |
| 6,540,672 | B1 | 4/2003 | Simonsen | 600/300 |
| 6,540,675 | B2 * | 4/2003 | Aceti et al. | 600/309 |
| 6,540,762 | B1 | 4/2003 | Bertling | 606/182 |
| 6,540,891 | B1 | 4/2003 | Stewart | 204/403.14 |
| 6,541,266 | B2 | 4/2003 | Modzelewski | 436/95 |
| 6,547,954 | B2 | 4/2003 | Ikeda | 205/777.5 |
| 6,549,796 | B2 | 4/2003 | Sohrab | 600/345 |
| 6,551,494 | B1 | 4/2003 | Heller et al. | 205/777.5 |
| 6,553,244 | B2 | 4/2003 | Lesho | 600/347 |
| 6,554,381 | B2 | 4/2003 | Locher | 347/7 |
| 6,555,061 | B1 | 4/2003 | Leong | 422/58 |
| D475,136 | S | 5/2003 | Taniguchi | D24/165 |
| 6,558,320 | B1 | 5/2003 | Causey | 600/300 |
| 6,558,361 | B1 | 5/2003 | Yeshurun | 604/272 |
| 6,558,402 | B1 | 5/2003 | Chelak | 606/182 |
| 6,558,528 | B1 | 5/2003 | Matzinger | 205/777.5 |
| 6,560,471 | B1 | 5/2003 | Heller | 600/347 |
| 6,561,978 | B1 | 5/2003 | Conn | 600/309 |
| 6,561,989 | B2 | 5/2003 | Whitson | 600/573 |
| 6,562,210 | B1 | 5/2003 | Bhullar | 204/403.3 |
| 6,565,509 | B1 | 5/2003 | Say | 600/365 |
| 6,565,808 | B2 | 5/2003 | Hudak | 422/58 |
| 6,569,157 | B1 | 5/2003 | Shain | 606/12 |
| 6,571,651 | B1 | 6/2003 | Hodges | 73/864.72 |
| 6,572,566 | B2 | 6/2003 | Effenhauser | 600/584 |
| 6,572,822 | B2 | 6/2003 | Jurik | 422/56 |
| 6,574,490 | B2 | 6/2003 | Abbink | 600/316 |
| 6,575,905 | B2 | 6/2003 | Knobbe | 600/365 |
| 6,576,101 | B1 | 6/2003 | Heller | 204/403.14 |
| 6,576,117 | B1 | 6/2003 | Iketaki et al. | 205/777.5 |
| 6,576,416 | B2 | 6/2003 | Haviland | 435/4 |
| 6,579,690 | B1 | 6/2003 | Bonnecaze et al. | 435/14 |
| 6,582,573 | B2 | 6/2003 | Douglas | 204/403.1 |
| 6,584,338 | B1 | 6/2003 | Van Muiswinkel | 600/419 |
| D477,670 | S | 7/2003 | Jurik | D24/225 |
| 6,586,199 | B2 | 7/2003 | Ouyang | 435/26 |
| 6,587,705 | B1 | 7/2003 | Kim | 600/347 |
| 6,589,260 | B1 | 7/2003 | Schmelzeisen-R | 606/181 |
| 6,589,261 | B1 | 7/2003 | Abulhaj | 606/181 |
| 6,591,124 | B2 | 7/2003 | Sherman | 600/345 |
| 6,591,125 | B1 | 7/2003 | Buse | 600/347 |
| 6,592,744 | B1 | 7/2003 | Hodges | 205/775 |
| 6,592,745 | B1 | 7/2003 | Feldman | 205/777.5 |
| 6,595,919 | B2 | 7/2003 | Berner | 600/365 |
| 6,599,407 | B2 | 7/2003 | Taniike | 204/403.1 |
| 6,599,693 | B1 | 7/2003 | Webb | 435/4 |
| 6,599,769 | B2 | 7/2003 | Kondo | 438/28 |
| 6,601,534 | B2 | 8/2003 | Hebrank | 119/6.8 |
| 6,602,205 | B1 | 8/2003 | Erickson | 600/573 |
| 6,602,268 | B2 | 8/2003 | Kuhr | 606/181 |
| 6,602,678 | B2 | 8/2003 | Kwon | 435/14 |
| 6,604,050 | B2 | 8/2003 | Trippel | 702/19 |
| 6,607,362 | B2 | 8/2003 | Lum | 417/53 |
| 6,607,494 | B1 | 8/2003 | Fowler | 600/570 |
| 6,607,658 | B1 | 8/2003 | Heller | 205/777.5 |
| 6,612,111 | B1 | 9/2003 | Hodges | 60/593 |
| 6,616,616 | B2 | 9/2003 | Fritz | 600/583 |
| 6,616,819 | B1 | 9/2003 | Liamos | 204/403.02 |
| 6,618,934 | B1 | 9/2003 | Feldman | 29/830 |
| 6,620,112 | B2 | 9/2003 | Klitmose | 600/583 |
| 6,620,310 | B1 | 9/2003 | Ohara | 205/792 |
| 6,623,501 | B2 | 9/2003 | Heller | 606/181 |
| 6,626,851 | B2 | 9/2003 | Hirao | 600/576 |
| 6,632,349 | B1 | 10/2003 | Hodges | 205/792 |
| 6,635,222 | B2 | 10/2003 | Kent | 422/22 |
| 6,638,415 | B1 | 10/2003 | Hodges | 205/775 |
| 6,638,772 | B1 | 10/2003 | Douglas | 436/518 |
| 6,641,533 | B2 | 11/2003 | Causey | 600/300 |
| 6,645,142 | B2 | 11/2003 | Braig | 600/300 |
| 6,645,219 | B2 | 11/2003 | Roe | 606/182 |
| 6,645,368 | B1 | 11/2003 | Beatty | 205/792 |
| 6,649,416 | B1 | 11/2003 | Kauer | 436/164 |
| 6,650,915 | B2 | 11/2003 | Routt | 600/319 |
| 6,652,720 | B1 | 11/2003 | Mansouri | 204/403.11 |
| 6,652,734 | B1 | 11/2003 | Hodges | 205/777.5 |
| 6,652,814 | B1 | 11/2003 | House | 422/104 |
| D484,600 | S | 12/2003 | Kaar | D24/169 |
| 6,656,697 | B1 | 12/2003 | Ouyang | 435/7.9 |
| 6,656,702 | B1 | 12/2003 | Yugawa | 435/26 |
| 6,659,966 | B2 | 12/2003 | Essenpreis | 600/583 |
| 6,660,018 | B2 | 12/2003 | Lum | 606/181 |
| 6,662,439 | B1 | 12/2003 | Bhullar | 29/825 |
| 6,669,669 | B2 | 12/2003 | Flaherty | 604/132 |
| 6,671,527 | B2 | 12/2003 | Peterson | 600/316 |
| D484,980 | S | 1/2004 | Hartwein | D24/165 |
| 6,673,617 | B2 | 1/2004 | Patel | 436/8 |
| 6,676,995 | B2 | 1/2004 | Dick | 427/286 |
| 6,679,841 | B2 | 1/2004 | Bojan | 600/309 |
| 6,679,852 | B1 | 1/2004 | Schmelzeisen-Redeker et al. | 600/583 |
| 6,682,933 | B2 | 1/2004 | Patel | 436/8 |
| 6,689,411 | B2 | 2/2004 | Dick | 427/2.13 |
| 6,706,000 | B2 | 3/2004 | Perez | 600/583 |
| 6,706,049 | B2 | 3/2004 | Moerman | 606/181 |
| 6,706,159 | B2 | 3/2004 | Moerman | 204/403.03 |
| 6,706,232 | B2 | 3/2004 | Hasegawa | 264/403.09 |
| 6,709,692 | B2 | 3/2004 | Sudor | 427/2.1 |
| 6,713,660 | B1 | 3/2004 | Roe | 604/361 |
| 6,716,577 | B1 | 4/2004 | Yu | 435/6 |
| 6,719,887 | B2 | 4/2004 | Hasegawa | 204/403.09 |
| 6,719,923 | B2 | 4/2004 | Stiene | 252/511 |
| 6,721,586 | B2 | 4/2004 | Kiser | 600/345 |
| 6,723,046 | B2 | 4/2004 | Lichtenstein | 600/300 |
| 6,723,111 | B2 | 4/2004 | Abulhaj | 606/181 |
| 6,723,371 | B2 | 4/2004 | Chih-hui | 472/2.13 |
| 6,723,500 | B2 | 4/2004 | Yu | 435/4 |
| 6,726,818 | B2 | 4/2004 | Cui et al. | 204/403.01 |
| 6,730,494 | B1 | 5/2004 | Toranto | 435/28 |
| 6,731,966 | B1 | 5/2004 | Spigelman | 600/407 |
| 6,733,493 | B2 | 5/2004 | Gruzdev | 606/9 |
| 6,736,777 | B2 | 5/2004 | Kim | 600/365 |
| 6,738,654 | B2 | 5/2004 | Sohrab | 600/345 |
| 6,740,215 | B1 | 5/2004 | Nakaminami | 204/403.14 |
| 6,743,211 | B1 | 6/2004 | Prausnitz et al. | 604/239 |
| 6,743,597 | B1 | 6/2004 | Guo | 435/14 |
| 6,743,635 | B2 | 6/2004 | Neel | 436/95 |
| 6,745,750 | B2 | 6/2004 | Egler et al. | 435/14 |
| 6,746,872 | B2 | 6/2004 | Zheng | 436/16 |
| 6,749,618 | B2 | 6/2004 | Levaughn | 606/182 |
| 6,749,740 | B2 | 6/2004 | Liamos | 205/792 |
| 6,749,792 | B2 | 6/2004 | Olsen | 264/328.1 |
| 6,749,887 | B1 | 6/2004 | Dick | 427/2.13 |
| 6,751,491 | B2 | 6/2004 | Lew | 600/345 |
| 6,752,817 | B2 | 6/2004 | Flora | 606/181 |
| 6,753,187 | B2 | 6/2004 | Cizdziel | 436/169 |
| 6,759,190 | B2 | 7/2004 | Lin | 435/4 |

| Patent | Date | Name | Ref |
|---|---|---|---|
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda et al. | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grubge | |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips et al. | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,829,507 B1 | 12/2004 | Lidman | 607/19 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,830,934 B1 | 12/2004 | Harding | 436/166 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,835,570 B2 | 12/2004 | Patel | 436/8 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,843,902 B1 | 1/2005 | Penner | 205/76 |
| 6,847,451 B2 | 1/2005 | Pugh | 356/436 |
| 6,849,052 B2 | 2/2005 | Uchigaki et al. | |
| 6,849,168 B2 | 2/2005 | Crumly et al. | 204/416 |
| 6,849,216 B2 | 2/2005 | Rappin | 264/134 |
| 6,849,456 B2 | 2/2005 | Patel | 436/8 |
| 6,850,790 B2 | 2/2005 | Berner | 600/347 |
| 6,852,119 B1 | 2/2005 | Abulhaj | 606/182 |
| 6,852,212 B2 | 2/2005 | Maxwell | 205/775 |
| 6,852,500 B1 | 2/2005 | Hoss | 435/14 |
| 6,853,854 B1 | 2/2005 | Proniewicz | 600/319 |
| 6,855,243 B2 | 2/2005 | Khan | 205/777.5 |
| 6,856,125 B2 | 2/2005 | Kermani | 324/71.1 |
| 6,856,928 B2 | 2/2005 | Harmon | 702/84 |
| 6,858,015 B2 | 2/2005 | List | 600/583 |
| 6,858,401 B2 | 2/2005 | Phillips | 435/14 |
| 6,859,738 B2 | 2/2005 | Bush | 702/25 |
| 6,862,466 B2 | 3/2005 | Ackerman | 600/347 |
| 6,862,534 B2 | 3/2005 | Sterling | 702/23 |
| 6,863,800 B2 | 3/2005 | Karinka | 205/777.5 |
| 6,863,801 B2 | 3/2005 | Hodges | 205/792 |
| 6,865,408 B1 | 3/2005 | Abbink | 600/310 |
| 6,866,641 B2 | 3/2005 | Marshall | 600/583 |
| 6,866,675 B2 | 3/2005 | Perez | 606/181 |
| 6,866,758 B2 | 3/2005 | Bhullar | 204/403.2 |
| 6,866,822 B1 | 3/2005 | House | 422/82.05 |
| 6,869,418 B2 | 3/2005 | Marano-Ford | 604/192 |
| 6,872,200 B2 | 3/2005 | Mann | 604/890.1 |
| 6,872,297 B2 | 3/2005 | Mansouri | 205/775 |
| 6,872,298 B2 | 3/2005 | Kermani | 205/777.5 |
| 6,872,299 B2 | 3/2005 | Kermani | 205/777.5 |
| 6,872,358 B2 | 3/2005 | Hagen | 422/61 |
| 6,875,208 B2 | 4/2005 | Santini | 604/890.1 |
| 6,875,223 B2 | 4/2005 | Argauer | 606/181 |
| 6,875,327 B1 | 4/2005 | Miyazaki | 204/403.14 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen et al. | |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,202 B2 | 5/2005 | Currie | 600/309 |
| 6,887,239 B2 | 5/2005 | Elstrom | 606/41 |
| 6,887,253 B2 | 5/2005 | Schraga | 606/181 |
| 6,887,254 B1 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russell | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,911,937 B1 | 6/2005 | Sparrow | 342/188 |
| 6,913,210 B2 | 7/2005 | Baasch | 239/407 |
| 6,913,668 B2 | 7/2005 | Matzinger | 156/256 |
| 6,916,410 B2 | 7/2005 | Katsuki | 204/403 |
| 6,918,901 B1 | 7/2005 | Theeuwes et al. | |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |

| Patent | Date | Name | Class |
|---|---|---|---|
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,960,323 B2 | 11/2005 | Guo | 422/60 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin et al. | |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/310 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,210 B2 | 5/2006 | Hodges | 205/792 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,043,821 B2 | 5/2006 | Hodges | 29/594 |
| 7,044,911 B2 | 5/2006 | Drinan | 600/300 |
| 7,045,046 B2 | 5/2006 | Chambers | 204/400 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,087 B2 | 5/2006 | Jenny | 435/13 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D522,656 S | 6/2006 | Orr | D24/169 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,059,352 B2 | 6/2006 | Bohm | 137/828 |
| 7,060,059 B2 | 6/2006 | Keith | 604/504 |
| 7,060,168 B2 | 6/2006 | Taniike | 204/403.04 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,079,252 B1 | 7/2006 | Debreezeny | 356/451 |

| Patent No. | Date | Name | Class |
|---|---|---|---|
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,006 B2 | 9/2006 | Schraga | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,113,172 B2 | 9/2006 | Hohl | 345/168 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,550 B2 | 11/2006 | Groth | 206/364 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,034 B2 | 11/2006 | Eppstein | 604/22 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,144,709 B2 | 12/2006 | Ouyang | 435/7.9 |
| 7,147,825 B2 | 12/2006 | Matsuda | 422/58 |
| 7,150,755 B2 | 12/2006 | Levaughn | 606/182 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,156,117 B2 | 1/2007 | Bohm | 137/14 |
| 7,156,810 B2 | 1/2007 | Cho | 600/365 |
| 7,157,723 B2 | 1/2007 | Colvin | 250/458.1 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,162,289 B2 | 1/2007 | Shah | 600/345 |
| 7,163,616 B2 | 1/2007 | Vreeke | 205/777.5 |
| 7,166,074 B2 | 1/2007 | Reghabi | 600/365 |
| 7,166,208 B2 | 1/2007 | Zweig | 205/777.5 |
| 7,167,734 B2 | 1/2007 | Khalil | 600/310 |
| 7,167,735 B2 | 1/2007 | Uchida | 600/310 |
| 7,167,818 B2 | 1/2007 | Brown | 703/11 |
| 7,169,116 B2 | 1/2007 | Day | 600/583 |
| 7,169,117 B2 | 1/2007 | Allen | 600/584 |
| 7,169,289 B2 | 1/2007 | Schulein | 205/777.5 |
| 7,169,600 B2 | 1/2007 | Hoss | 435/287.1 |
| 7,172,728 B2 | 2/2007 | Otake | 422/58 |
| 7,174,199 B2 | 2/2007 | Berner | 600/347 |
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,102 B2 | 2/2007 | Monfre et al. | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson et al. | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erikson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman et al. | |
| 7,226,414 B2 | 6/2007 | Ballerstadt | 600/365 |
| 7,226,461 B2 | 6/2007 | Boecker et al. | |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Freeman | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 7,238,192 B2 | 7/2007 | List | 606/182 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,138 B2 | 7/2007 | Reghabi | 600/365 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,513 B2 | 7/2007 | Kondoh | 600/310 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |

| Patent No. | Date | Name | Class |
|---|---|---|---|
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin | 600/316 |
| 7,291,117 B2 | 11/2007 | Boecker | 600/583 |
| 7,291,159 B2 | 11/2007 | Schmelzeisen-Redeker et al. | 606/181 |
| 7,291,256 B2 | 11/2007 | Teodorczyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |
| 7,297,122 B2 | 11/2007 | Boecker | 600/583 |
| 7,297,151 B2 | 11/2007 | Boecker | 606/181 |
| 7,297,152 B2 | 11/2007 | Fukuzawa | 606/181 |
| 7,297,241 B2 | 11/2007 | Kontschieder | 204/403.01 |
| 7,297,248 B2 | 11/2007 | Bae | 205/777.5 |
| 7,297,627 B2 | 11/2007 | Shah | 438/622 |
| 7,299,079 B2 | 11/2007 | Rebec | 600/316 |
| 7,299,080 B2 | 11/2007 | Acosta | 600/316 |
| 7,299,081 B2 | 11/2007 | Mace | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/316 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,324,012 B2 | 1/2008 | Mann | 340/870.07 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/309 |
| 7,344,500 B2 | 3/2008 | Talbot | 600/365 |
| 7,344,507 B2 | 3/2008 | Briggs | 600/583 |
| 7,344,626 B2 | 3/2008 | Harding | 204/403.01 |
| 7,347,925 B2 | 3/2008 | Hsieh | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | 205/777.5 |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Schartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,720 B2 | 5/2008 | Fu | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/792 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/78 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |

| | | | |
|---|---|---|---|
| D612,275 S | 3/2010 | Salter .................... D10/81 |
| D612,279 S | 3/2010 | Heidemann ................ D10/103 |
| 7,674,232 B2 | 3/2010 | Boecker .................. 600/583 |
| 7,682,318 B2 | 3/2010 | Alden .................... 600/583 |
| 7,713,214 B2 | 5/2010 | Freeman et al. ........... 600/583 |
| 2001/0017269 A1 | 8/2001 | Heller ................... 205/777.5 |
| 2001/0027328 A1 | 10/2001 | Lum ..................... 606/186 |
| 2001/0031931 A1 | 10/2001 | Cunningham .............. 600/573 |
| 2001/0037355 A1 | 11/2001 | Britt .................... 709/201 |
| 2001/0042004 A1 | 11/2001 | Taub .................... 705/11 |
| 2001/0045355 A1 | 11/2001 | Gephart .................. 204/400 |
| 2001/0054319 A1 | 12/2001 | Heller ................... 73/849 |
| 2002/0002326 A1 | 1/2002 | Causey ................... 600/300 |
| 2002/0002344 A1 | 1/2002 | Douglas .................. 600/583 |
| 2002/0004196 A1 | 1/2002 | Whitson .................. 600/573 |
| 2002/0016568 A1 | 2/2002 | Lebel .................... 604/131 |
| 2002/0016923 A1 | 2/2002 | Knaus .................... 713/200 |
| 2002/0019606 A1 | 2/2002 | Lebel .................... 604/66 |
| 2002/0019747 A1 | 2/2002 | Ware ..................... 705/2 |
| 2002/0025469 A1 | 2/2002 | Heller ................... 429/43 |
| 2002/0029058 A1 | 3/2002 | Levaughn ................. 606/181 |
| 2002/0040208 A1 | 4/2002 | Flaherty ................. 604/288.01 |
| 2002/0040230 A1 | 4/2002 | Kuhr ..................... 606/181 |
| 2002/0042090 A1 | 4/2002 | Heller ................... 435/14 |
| 2002/0042594 A1 | 4/2002 | Lum et al. |
| 2002/0044890 A1 | 4/2002 | Black .................... 422/56 |
| 2002/0052618 A1 | 5/2002 | Haar et al. |
| 2002/0053523 A1 | 5/2002 | Liamos ................... 205/787 |
| 2002/0057993 A1 | 5/2002 | Maisey ................... 422/82.01 |
| 2002/0076349 A1 | 6/2002 | Aitken ................... 422/58 |
| 2002/0078091 A1 | 6/2002 | Vu ....................... 707/513 |
| 2002/0081588 A1 | 6/2002 | Lumley-Woodyear .......... 435/6 |
| 2002/0082543 A1 | 6/2002 | Park ..................... 604/21 |
| 2002/0084196 A1 | 7/2002 | Liamos ................... 205/792 |
| 2002/0087056 A1 | 7/2002 | Aceti |
| 2002/0092612 A1 | 7/2002 | Davies ................... 156/292 |
| 2002/0099308 A1 | 7/2002 | Bojan et al. |
| 2002/0103499 A1 | 8/2002 | Perez .................... 606/182 |
| 2002/0120216 A1 | 8/2002 | Fritz .................... 600/583 |
| 2002/0123335 A1 | 9/2002 | Luna ..................... 455/419 |
| 2002/0130042 A1 | 9/2002 | Moerman et al. .......... 204/403.01 |
| 2002/0136667 A1 | 9/2002 | Subramanian .............. 422/100 |
| 2002/0136863 A1 | 9/2002 | Subramanian et al. ....... 428/156 |
| 2002/0137998 A1 | 9/2002 | Smart .................... 600/347 |
| 2002/0148739 A2 | 10/2002 | Liamos ................... 205/787 |
| 2002/0160520 A1 | 10/2002 | Orloff ................... 436/72 |
| 2002/0161289 A1 | 10/2002 | Hopkins .................. 600/322 |
| 2002/0168290 A1 | 11/2002 | Yuzhakov ................. 422/56 |
| 2002/0169393 A1 | 11/2002 | Cunningham ............... 600/573 |
| 2002/0169394 A1 | 11/2002 | Eppstein ................. 600/573 |
| 2002/0176984 A1 | 11/2002 | Smart .................... 428/336 |
| 2002/0177761 A1 | 11/2002 | Orloff ................... 600/309 |
| 2002/0177763 A1 | 11/2002 | Burns .................... 600/345 |
| 2002/0188224 A1 | 12/2002 | Roe ...................... 600/584 |
| 2003/0014010 A1 | 1/2003 | Carpenter ................ 604/117 |
| 2003/0018282 A1 | 1/2003 | Effenhauser .............. 600/583 |
| 2003/0018300 A1 | 1/2003 | Duchon ................... 604/164.01 |
| 2003/0028126 A1 | 2/2003 | List ..................... 600/583 |
| 2003/0032077 A1 | 2/2003 | Itoh ..................... 435/14 |
| 2003/0038047 A1 | 2/2003 | Sleva .................... 206/370 |
| 2003/0050573 A1 | 3/2003 | Kuhr ..................... 600/567 |
| 2003/0050656 A1 | 3/2003 | Schraga .................. 606/182 |
| 2003/0057391 A1 | 3/2003 | Krulevitch ............... 251/11 |
| 2003/0060730 A1 | 3/2003 | Perez .................... 600/576 |
| 2003/0072647 A1 | 4/2003 | Lum ...................... 415/1 |
| 2003/0073089 A1 | 4/2003 | Mauze .................... 435/6 |
| 2003/0073229 A1 | 4/2003 | Greenstein ............... 435/287.2 |
| 2003/0073931 A1 | 4/2003 | Boecker et al. |
| 2003/0083685 A1 | 5/2003 | Freeman .................. 606/181 |
| 2003/0083686 A1 | 5/2003 | Freeman |
| 2003/0088191 A1 | 5/2003 | Freeman et al. ........... 600/583 |
| 2003/0089730 A1 | 5/2003 | May ...................... 221/232 |
| 2003/0093010 A1 | 5/2003 | Essenpreis ............... 600/583 |
| 2003/0100040 A1 | 5/2003 | Bonnecaze ................ 435/14 |
| 2003/0106810 A1 | 6/2003 | Douglas .................. 205/777.5 |
| 2003/0109777 A1 | 6/2003 | Kloepfer ................. 600/367 |
| 2003/0109860 A1 | 6/2003 | Black |
| 2003/0111357 A1 | 6/2003 | Black .................... 205/775 |
| 2003/0113827 A1 | 6/2003 | Burkoth .................. 435/14 |
| 2003/0116447 A1 | 6/2003 | Sturridge ................ 205/777.5 |
| 2003/0120297 A1 | 6/2003 | Beyerlein ................ 606/185 |
| 2003/0135333 A1 | 7/2003 | Aceti .................... 702/31 |
| 2003/0136189 A1 | 7/2003 | Lauman et al. |
| 2003/0143113 A2 | 7/2003 | Yuzhakov ................. 422/56 |
| 2003/0144608 A1 | 7/2003 | Kojima ................... 600/583 |
| 2003/0144609 A1 | 7/2003 | Kennedy .................. 600/583 |
| 2003/0146110 A1 | 8/2003 | Karinka .................. 205/777.5 |
| 2003/0149348 A1 | 8/2003 | Raskas ................... 600/310 |
| 2003/0149377 A1 | 8/2003 | Erickson ................. 600/573 |
| 2003/0153900 A1 | 8/2003 | Aceti .................... 604/890.1 |
| 2003/0191376 A1 | 10/2003 | Samuels .................. 600/309 |
| 2003/0191415 A1 | 10/2003 | Moerman .................. 600/584 |
| 2003/0195435 A1 | 10/2003 | Williams ................. 600/583 |
| 2003/0195540 A1 | 10/2003 | Moerman .................. 606/181 |
| 2003/0199744 A1 | 10/2003 | Buse ..................... 600/347 |
| 2003/0199789 A1 | 10/2003 | Boecker .................. 600/575 |
| 2003/0199790 A1 | 10/2003 | Boecker .................. 600/576 |
| 2003/0199791 A1 | 10/2003 | Boecker .................. 600/576 |
| 2003/0199891 A1 | 10/2003 | Argauer .................. 606/181 |
| 2003/0199893 A1 | 10/2003 | Boecker .................. 606/181 |
| 2003/0199894 A1 | 10/2003 | Boecker .................. 606/181 |
| 2003/0199896 A1 | 10/2003 | Boecker .................. 606/181 |
| 2003/0199897 A1 | 10/2003 | Boecker .................. 606/181 |
| 2003/0199898 A1 | 10/2003 | Boecker .................. 606/181 |
| 2003/0199899 A1 | 10/2003 | Boecker .................. 606/181 |
| 2003/0199900 A1 | 10/2003 | Boecker .................. 606/181 |
| 2003/0199901 A1 | 10/2003 | Boecker .................. 606/181 |
| 2003/0199902 A1 | 10/2003 | Boecker .................. 606/181 |
| 2003/0199903 A1 | 10/2003 | Boecker .................. 606/181 |
| 2003/0199904 A1 | 10/2003 | Boecker .................. 606/181 |
| 2003/0199905 A1 | 10/2003 | Boecker .................. 606/181 |
| 2003/0199906 A1 | 10/2003 | Boecker .................. 606/181 |
| 2003/0199907 A1 | 10/2003 | Boecker .................. 606/181 |
| 2003/0199908 A1 | 10/2003 | Boecker .................. 606/181 |
| 2003/0199909 A1 | 10/2003 | Boecker .................. 606/181 |
| 2003/0199910 A1 | 10/2003 | Boecker .................. 606/181 |
| 2003/0199911 A1 | 10/2003 | Boecker .................. 606/181 |
| 2003/0199912 A1 | 10/2003 | Pugh ..................... 606/182 |
| 2003/0201194 A1 | 10/2003 | Heller ................... 205/777.5 |
| 2003/0203352 A1 | 10/2003 | Haviland ................. 435/4 |
| 2003/0206828 A1 | 11/2003 | Bell ..................... 422/44 |
| 2003/0208140 A1 | 11/2003 | Pugh ..................... 600/584 |
| 2003/0210811 A1 | 11/2003 | Dubowsky ................. 382/128 |
| 2003/0212344 A1 | 11/2003 | Yuzhakov ................. 600/583 |
| 2003/0212345 A1 | 11/2003 | McAllister ............... 600/584 |
| 2003/0212346 A1 | 11/2003 | McAllister et al. ........ 600/584 |
| 2003/0212347 A1 | 11/2003 | Sohrab ................... 600/584 |
| 2003/0212379 A1 | 11/2003 | Bylund ................... 604/504 |
| 2003/0212423 A1 | 11/2003 | Pugh ..................... 606/181 |
| 2003/0212424 A1 | 11/2003 | Briggs ................... 606/181 |
| 2003/0216767 A1 | 11/2003 | List ..................... 606/181 |
| 2003/0217918 A1 | 11/2003 | Davies ................... 204/403.14 |
| 2003/0220552 A1 | 11/2003 | Reghabi .................. 600/365 |
| 2003/0220663 A1 | 11/2003 | Fletcher ................. 606/182 |
| 2003/0223906 A1 | 12/2003 | McAllister ............... 422/58 |
| 2003/0225429 A1 | 12/2003 | Garthe ................... 606/182 |
| 2003/0225430 A1 | 12/2003 | Schraga .................. 606/182 |
| 2003/0228637 A1 | 12/2003 | Wang ..................... 435/7.9 |
| 2003/0232370 A1 | 12/2003 | Trifiro .................. 435/6 |
| 2003/0233055 A1 | 12/2003 | Erickson ................. 600/573 |
| 2003/0233112 A1 | 12/2003 | Alden et al. ............. 606/181 |
| 2003/0233113 A1 | 12/2003 | Alden et al. ............. 606/182 |
| 2004/0006285 A1 | 1/2004 | Douglas .................. 600/583 |
| 2004/0007585 A1 | 1/2004 | Griffith ................. 221/232 |
| 2004/0009100 A1 | 1/2004 | Simons ................... 422/102 |
| 2004/0010279 A1 | 1/2004 | Freeman .................. 606/182 |
| 2004/0015064 A1 | 1/2004 | Parsons .................. 600/347 |
| 2004/0019250 A1 | 1/2004 | Catelli .................. 600/1 |
| 2004/0026243 A1 | 2/2004 | Davies ................... 204/403.14 |
| 2004/0026244 A1 | 2/2004 | Hodges ................... 204/409 |
| 2004/0030353 A1 | 2/2004 | Schmelzeisen-Redeker et al. .................... 606/201 |
| 2004/0031682 A1 | 2/2004 | Wilsey ................... 204/403.1 |
| 2004/0034318 A1 | 2/2004 | Fritz et al. ............. 604/19 |
| 2004/0038045 A1 | 2/2004 | Smart .................... 428/446 |
| 2004/0039303 A1 | 2/2004 | Wurster .................. 600/584 |
| 2004/0039342 A1 | 2/2004 | Eppstein ................. 604/200 |
| 2004/0039407 A1 | 2/2004 | Schraga .................. 606/181 |

| Pub. No. | Date | Inventor | Class |
|---|---|---|---|
| 2004/0039408 A1 | 2/2004 | Abulhaj | 606/181 |
| 2004/0256228 A1 | 2/2004 | Huang | 204/434 |
| 2004/0049220 A1 | 3/2004 | Boecker | 606/181 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0069657 A1 | 4/2004 | Hodges | 205/787 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Kheiri | 606/182 |
| 2004/0167383 A1 | 8/2004 | Kim | 600/365 |
| 2004/0171057 A1 | 9/2004 | Yang et al. | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/185 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231983 A1 | 11/2004 | Shen | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/250 |
| 2004/0236251 A1 | 11/2004 | Roe | 600/583 |
| 2004/0236268 A1 | 11/2004 | Mitragotri | 604/20 |
| 2004/0236362 A1 | 11/2004 | Shraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |

| Publication No. | Date | Name | Class |
|---|---|---|---|
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara et al. | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/22 |
| 2005/0043965 A1 | 2/2005 | Heller | 705/2 |
| 2005/0045476 A1 | 3/2005 | Neel | 204/403.2 |
| 2005/0049472 A1 | 3/2005 | Manda | 600/345 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman | 204/403.01 |
| 2005/0064528 A1 | 3/2005 | Kwon | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini, Jr. | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Prausnitz et al. | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0149090 A1 | 7/2005 | Morita et al. | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169810 A1 | 8/2005 | Hagen | 422/102 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0176153 A1 | 8/2005 | O'hara | 436/70 |
| 2005/0177071 A1 | 8/2005 | Nakayama | 600/583 |
| 2005/0177201 A1 | 8/2005 | Freeman | 607/46 |
| 2005/0177213 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Salto | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |

| Publication No. | Date | Name | Class |
|---|---|---|---|
| 2005/0203364 A1 | 9/2005 | Monfre | 600/365 |
| 2005/0204939 A1 | 9/2005 | Krejci | 101/129 |
| 2005/0205136 A1 | 9/2005 | Freeman | 137/554 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/200 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030050 A1 | 2/2006 | Milne | 436/67 |
| 2006/0030761 A1 | 2/2006 | Raskas | 600/316 |
| 2006/0030788 A1 | 2/2006 | Wong | 600/583 |
| 2006/0034728 A1 | 2/2006 | Kloepfer | 422/68.1 |
| 2006/0037859 A1 | 2/2006 | Hodges | 204/400 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang et al. | 204/403.02 |
| 2006/0094944 A1 | 5/2006 | Chuang | 600/347 |
| 2006/0094947 A1 | 5/2006 | Kovatchev | 600/365 |
| 2006/0094985 A1 | 5/2006 | Aceti | 600/575 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0160100 A1 | 7/2006 | Gao | 435/6 |
| 2006/0161078 A1 | 7/2006 | Schraga | 600/583 |
| 2006/0161194 A1 | 7/2006 | Freeman | 606/185 |
| 2006/0163061 A1 | 7/2006 | Hodges | 204/401 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |

| Pub. No. | Date | Inventor | Class |
|---|---|---|---|
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184065 A1 | 8/2006 | Deshmukh | 600/583 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0201804 A1 | 9/2006 | Chambers | 204/400 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0231442 A1 | 10/2006 | Windus-Smith | 206/438 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247154 A1 | 11/2006 | Palmieri | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0254932 A1 | 11/2006 | Hodges | 205/775 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0266644 A1 | 11/2006 | Pugh | 204/400 |
| 2006/0266765 A1 | 11/2006 | Pugh | 222/1 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0279431 A1 | 12/2006 | Bakarania | 340/870.02 |
| 2006/0281187 A1 | 12/2006 | Emery | 436/169 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman et al. | |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Moore | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |

| | | | |
|---|---|---|---|
| 2007/0119710 A1 | 5/2007 | Golberger .............. 204/403.01 |
| 2007/0123801 A1 | 5/2007 | Golberger .................. 600/583 |
| 2007/0123802 A1 | 5/2007 | Freeman .................... 600/583 |
| 2007/0129618 A1 | 6/2007 | Golberger .................. 600/345 |
| 2007/0129650 A1 | 6/2007 | Freeman et al. |
| 2007/0131565 A1 | 6/2007 | Fujiwara .................. 205/777.5 |
| 2007/0135828 A1 | 6/2007 | Rutynowski .............. 606/181 |
| 2007/0142747 A1 | 6/2007 | Boecker .................... 600/583 |
| 2007/0142748 A1 | 6/2007 | Deshmukh et al. |
| 2007/0142776 A9 | 6/2007 | Kovelman ................. 604/136 |
| 2007/0142854 A1 | 6/2007 | Schraga .................... 606/181 |
| 2007/0144235 A1 | 6/2007 | Werner ....................... 73/1.82 |
| 2007/0149875 A1 | 6/2007 | Ouyang ..................... 600/347 |
| 2007/0149897 A1 | 6/2007 | Ghesquiere ............... 600/583 |
| 2007/0161960 A1 | 7/2007 | Chen ......................... 604/187 |
| 2007/0162064 A1 | 7/2007 | Starnes ...................... 606/181 |
| 2007/0162065 A1 | 7/2007 | Li ............................... 606/182 |
| 2007/0167869 A1 | 7/2007 | Roe ............................ 600/583 |
| 2007/0167870 A1 | 7/2007 | Freeman .................... 600/583 |
| 2007/0167871 A1 | 7/2007 | Freeman .................... 600/583 |
| 2007/0167872 A1 | 7/2007 | Freeman .................... 600/583 |
| 2007/0167873 A1 | 7/2007 | Freeman .................... 600/583 |
| 2007/0167874 A1 | 7/2007 | Freeman .................... 600/583 |
| 2007/0167875 A1 | 7/2007 | Freeman .................... 600/583 |
| 2007/0173739 A1 | 7/2007 | Chan .......................... 600/583 |
| 2007/0173740 A1 | 7/2007 | Chan .......................... 600/583 |
| 2007/0173741 A1 | 7/2007 | Deshmukh et al. |
| 2007/0173742 A1 | 7/2007 | Freeman et al. .......... 600/583 |
| 2007/0173743 A1 | 7/2007 | Freeman .................... 600/583 |
| 2007/0173874 A1 | 7/2007 | Uschold ..................... 606/181 |
| 2007/0173875 A1 | 7/2007 | Uschold ..................... 606/181 |
| 2007/0173876 A1 | 7/2007 | Aylett ........................ 606/181 |
| 2007/0176120 A1 | 8/2007 | Schwind et al. ......... 250/492.1 |
| 2007/0179356 A1 | 8/2007 | Wessel ....................... 600/300 |
| 2007/0179404 A1 | 8/2007 | Escutia ...................... 600/583 |
| 2007/0179405 A1 | 8/2007 | Emery ....................... 600/583 |
| 2007/0179406 A1 | 8/2007 | DeNuzzio .................. 600/583 |
| 2007/0182051 A1 | 8/2007 | Harttig ....................... 264/138 |
| 2007/0185412 A1 | 8/2007 | Boecker ..................... 600/583 |
| 2007/0185515 A1 | 8/2007 | Stout .......................... 606/181 |
| 2007/0185516 A1 | 8/2007 | Schosnig .................... 606/181 |
| 2007/0191702 A1 | 8/2007 | Yodfat ........................ 600/365 |
| 2007/0191737 A1 | 8/2007 | Freeman .................... 600/583 |
| 2007/0191738 A1 | 8/2007 | Raney ........................ 600/583 |
| 2007/0191739 A1 | 8/2007 | Roe ............................ 600/583 |
| 2007/0193019 A1 | 8/2007 | Feldman .................... 29/592.1 |
| 2007/0193882 A1 | 8/2007 | Dai ........................... 204/403.02 |
| 2007/0196240 A1 | 8/2007 | Boozer ....................... 422/102 |
| 2007/0196242 A1 | 8/2007 | Boozer ....................... 422/102 |
| 2007/0203514 A1 | 8/2007 | Flaherty ..................... 606/181 |
| 2007/0203903 A1 | 8/2007 | Attaran Rezaei ............ 707/5 |
| 2007/0205103 A1 | 9/2007 | Hodges ................... 204/403.01 |
| 2007/0207498 A1 | 9/2007 | Palmieri ..................... 435/7.1 |
| 2007/0213601 A1 | 9/2007 | Freeman .................... 600/300 |
| 2007/0213637 A1 | 9/2007 | Boozer ....................... 600/583 |
| 2007/0213682 A1 | 9/2007 | Haar ........................... 604/500 |
| 2007/0213756 A1 | 9/2007 | Freeman .................... 606/181 |
| 2007/0218543 A1 | 9/2007 | Flaherty ..................... 435/287.1 |
| 2007/0219346 A1 | 9/2007 | Trifiro ........................ 530/308 |
| 2007/0219432 A1 | 9/2007 | Thompson ................. 600/300 |
| 2007/0219436 A1 | 9/2007 | Takase ....................... 600/310 |
| 2007/0219462 A1 | 9/2007 | Briggs ........................ 600/583 |
| 2007/0219463 A1 | 9/2007 | Briggs ........................ 600/583 |
| 2007/0219572 A1 | 9/2007 | Deck .......................... 606/181 |
| 2007/0219573 A1 | 9/2007 | Freeman .................... 606/183 |
| 2007/0219574 A1 | 9/2007 | Freeman .................... 606/185 |
| 2007/0225741 A1 | 9/2007 | Ikeda ......................... 606/182 |
| 2007/0225742 A1 | 9/2007 | Abe ............................ 606/182 |
| 2007/0227907 A1 | 10/2007 | Shah ......................... 205/777.5 |
| 2007/0227911 A1 | 10/2007 | Wang ......................... 205/792 |
| 2007/0227912 A1 | 10/2007 | Chatelier .................... 205/792 |
| 2007/0229085 A1 | 10/2007 | Kawai ........................ 324/450 |
| 2007/0232872 A1 | 10/2007 | Prough ....................... 600/316 |
| 2007/0232956 A1 | 10/2007 | Harman ...................... 600/573 |
| 2007/0233013 A1 | 10/2007 | Schoenberg ................ 604/192 |
| 2007/0233166 A1 | 10/2007 | Stout .......................... 606/182 |
| 2007/0233167 A1 | 10/2007 | Weiss ......................... 606/182 |
| 2007/0233395 A1 | 10/2007 | Neel ........................... 702/19 |
| 2007/0235329 A1 | 10/2007 | Harding ................... 204/403.01 |
| 2007/0235347 A1 | 10/2007 | Chatelier .................... 205/792 |
| 2007/0239068 A1 | 10/2007 | Rasch-Menges ........... 600/573 |
| 2007/0239188 A1 | 10/2007 | Boozer ....................... 606/181 |
| 2007/0239189 A1 | 10/2007 | Freeman .................... 606/181 |
| 2007/0239190 A1 | 10/2007 | Alden ........................ 606/181 |
| 2007/0240984 A1 | 10/2007 | Popovich ................... 204/403.01 |
| 2007/0240986 A1 | 10/2007 | Reymond ................... 204/412 |
| 2007/0244380 A1 | 10/2007 | Say ............................ 600/347 |
| 2007/0244412 A1 | 10/2007 | Lav ............................ 600/584 |
| 2007/0244498 A1 | 10/2007 | Steg ........................... 606/181 |
| 2007/0244499 A1 | 10/2007 | Briggs ........................ 606/182 |
| 2007/0249921 A1 | 10/2007 | Groll .......................... 600/347 |
| 2007/0249962 A1 | 10/2007 | Alden ........................ 600/583 |
| 2007/0249963 A1 | 10/2007 | Alden ........................ 600/583 |
| 2007/0250099 A1 | 10/2007 | Flora .......................... 606/181 |
| 2007/0251836 A1 | 11/2007 | Hsu ............................ 205/792 |
| 2007/0254359 A1 | 11/2007 | Rezania ...................... 435/325 |
| 2007/0255141 A1 | 11/2007 | Esenaliev ................... 600/475 |
| 2007/0255178 A1 | 11/2007 | Alvarez-Icaza ............. 600/583 |
| 2007/0255179 A1 | 11/2007 | Alvarez-Icaza ............. 600/583 |
| 2007/0255180 A1 | 11/2007 | Alvarez-Icaza ............. 600/583 |
| 2007/0255181 A1 | 11/2007 | Alvarez-Icaza ............. 600/583 |
| 2007/0255300 A1 | 11/2007 | Vanhiel ...................... 606/181 |
| 2007/0255301 A1 | 11/2007 | Freeman .................... 606/181 |
| 2007/0255302 A1 | 11/2007 | Koeppel .................... 606/182 |
| 2007/0260271 A1 | 11/2007 | Freeman .................... 606/181 |
| 2007/0260272 A1 | 11/2007 | Weiss ......................... 606/181 |
| 2007/0264721 A1 | 11/2007 | Buck .......................... 436/150 |
| 2007/0265511 A1 | 11/2007 | Renouf ....................... 600/319 |
| 2007/0265532 A1 | 11/2007 | Maynard .................... 600/477 |
| 2007/0265654 A1 | 11/2007 | Iio ............................... 606/185 |
| 2007/0273901 A1 | 11/2007 | Baskeyfield ................ 358/1.9 |
| 2007/0273903 A1 | 11/2007 | Baskeyfield ................ 358/1.9 |
| 2007/0273904 A1 | 11/2007 | Robinson ................... 358/1.9 |
| 2007/0273928 A1 | 11/2007 | Robinson ................... 358/1.9 |
| 2007/0276197 A1 | 11/2007 | Harmon ...................... 600/300 |
| 2007/0276211 A1 | 11/2007 | Mir ............................ 600/345 |
| 2007/0276290 A1 | 11/2007 | Boecker et al. |
| 2007/0276425 A1 | 11/2007 | Kim ............................ 606/186 |
| 2007/0276621 A1 | 11/2007 | Davies ....................... 702/104 |
| 2007/0278097 A1 | 12/2007 | Bhullar ..................... 204/403.01 |
| 2007/0282186 A1 | 12/2007 | Gilmore ..................... 600/365 |
| 2007/0282362 A1 | 12/2007 | Berg .......................... 606/181 |
| 2007/0288047 A1 | 12/2007 | Thoes ........................ 606/182 |
| 2007/0293743 A1 | 12/2007 | Monfre ...................... 600/316 |
| 2007/0293744 A1 | 12/2007 | Monfre ...................... 600/316 |
| 2007/0293790 A1 | 12/2007 | Bainczyk ................... 600/583 |
| 2007/0293882 A1 | 12/2007 | Harttig ....................... 606/181 |
| 2007/0293883 A1 | 12/2007 | Horie ......................... 606/181 |
| 2007/0295616 A1 | 12/2007 | Harding ..................... 205/777.5 |
| 2008/0004651 A1 | 1/2008 | Nicholls ..................... 606/182 |
| 2008/0007141 A1 | 1/2008 | Deck .......................... 310/328 |
| 2008/0009767 A1 | 1/2008 | Effenhauser ............... 600/583 |
| 2008/0009768 A1 | 1/2008 | Sohrab ....................... 600/583 |
| 2008/0009892 A1 | 1/2008 | Freeman .................... 606/181 |
| 2008/0009893 A1 | 1/2008 | LeVaughn ................. 606/181 |
| 2008/0015425 A1 | 1/2008 | Douglas ..................... 600/347 |
| 2008/0015623 A1 | 1/2008 | Deck .......................... 606/181 |
| 2008/0017522 A1 | 1/2008 | Heller ........................ 205/777.5 |
| 2008/0019870 A1 | 1/2008 | Newman .................... 422/68.1 |
| 2008/0021291 A1 | 1/2008 | Zocchi ....................... 600/300 |
| 2008/0021293 A1 | 1/2008 | Schurman ................... 600/316 |
| 2008/0021295 A1 | 1/2008 | Wang ......................... 600/347 |
| 2008/0021296 A1 | 1/2008 | Creaven ..................... 600/365 |
| 2008/0021346 A1 | 1/2008 | Haar ........................... 600/583 |
| 2008/0021490 A1 | 1/2008 | Briggs ........................ 606/181 |
| 2008/0021491 A1 | 1/2008 | Freeman .................... 606/181 |
| 2008/0021492 A1 | 1/2008 | Freeman .................... 606/181 |
| 2008/0021493 A1 | 1/2008 | Levaughn ................... 606/181 |
| 2008/0021494 A1 | 1/2008 | Schmelzeisen-R .......... 606/181 |
| 2008/0027385 A1 | 1/2008 | Freeman .................... 604/117 |
| 2008/0031778 A1 | 2/2008 | Kramer ...................... 422/68.1 |
| 2008/0033268 A1 | 2/2008 | Stafford ..................... 600/345 |
| 2008/0033318 A1 | 2/2008 | Mace ......................... 600/583 |
| 2008/0033319 A1 | 2/2008 | Kloepfer .................... 600/583 |
| 2008/0033468 A1 | 2/2008 | Lathrop ...................... 606/181 |
| 2008/0033469 A1 | 2/2008 | Winheim .................... 606/181 |
| 2008/0034834 A1 | 2/2008 | Schell ......................... 73/1.02 |
| 2008/0034835 A1 | 2/2008 | Schell ......................... 73/1.02 |

| Publication No. | Date | Name | Class |
|---|---|---|---|
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee et al. | |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 702/19 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/347 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | |
| 2008/0194989 A1 | 8/2008 | Briggs | 600/583 |
| 2008/0208026 A1 | 8/2008 | Noujaim | 600/365 |
| 2008/0208079 A1 | 8/2008 | Hein | 600/575 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275675 A1 | 11/2008 | Guthrie | 600/584 |
| 2008/0275384 A1 | 11/2008 | Mastrototaro | 604/66 |
| 2008/0277291 A1 | 11/2008 | Heller | 205/777.5 |
| 2008/0277292 A1 | 11/2008 | Heller | 205/777.5 |
| 2008/0277293 A1 | 11/2008 | Heller | 205/777.5 |
| 2008/0277294 A1 | 11/2008 | Heller | 205/777.5 |
| 2008/0286149 A1 | 11/2008 | Roe | 422/58 |
| 2008/0294068 A1 | 11/2008 | Briggs | 600/583 |
| 2008/0300614 A1 | 12/2008 | Freeman | 606/181 |
| 2008/0318193 A1 | 12/2008 | Alvarez-Icaza | 434/262 |
| 2008/0319284 A1 | 12/2008 | Alvarez-Icaza | 600/309 |
| 2008/0319291 A1 | 12/2008 | Freeman | 600/347 |
| 2009/0005664 A1 | 1/2009 | Freeman | 600/347 |
| 2009/0020438 A1 | 1/2009 | Hodges | 205/782 |
| 2009/0024009 A1 | 1/2009 | Freeman | 600/309 |
| 2009/0024059 A1 | 1/2009 | Hoerauf | 600/583 |
| 2009/0026075 A1 | 1/2009 | Harding | 204/403.14 |
| 2009/0026091 A1 | 1/2009 | Harding | 205/777.5 |
| 2009/0027040 A1 | 1/2009 | Kermani | 324/123 |
| 2009/0029479 A1 | 1/2009 | Docherty | 436/149 |
| 2009/0043177 A1 | 2/2009 | Milledge | 600/309 |
| 2009/0043183 A1 | 2/2009 | Kermani | 600/365 |
| 2009/0048536 A1 | 2/2009 | Freeman | 600/583 |
| 2009/0054813 A1 | 2/2009 | Freeman | 600/584 |
| 2009/0057146 A1 | 3/2009 | Teodorczyk | 204/403.01 |
| 2009/0069716 A1 | 3/2009 | Freeman | 600/583 |
| 2009/0084687 A1 | 4/2009 | Chatelier | 205/792 |
| 2009/0105572 A1 | 4/2009 | Malecha | 600/365 |
| 2009/0105585 A1 | 4/2009 | Malecha | 600/365 |
| 2009/0112123 A1 | 4/2009 | Freeman | 600/583 |
| 2009/0112155 A1 | 4/2009 | Zhao | 604/67 |
| 2009/0112180 A1 | 4/2009 | Krulevitch | 604/506 |
| 2009/0112185 A1 | 4/2009 | Krulevitch | 604/523 |
| 2009/0124932 A1 | 5/2009 | Freeman | 606/181 |
| 2009/0131829 A1 | 5/2009 | Freeman | 600/583 |
| 2009/0131830 A1 | 5/2009 | Freeman | 600/583 |
| 2009/0131964 A1 | 5/2009 | Freeman | 606/181 |
| 2009/0131965 A1 | 5/2009 | Freeman | 606/181 |
| 2009/0137930 A1 | 5/2009 | Freeman | 600/583 |
| 2009/0138032 A1 | 5/2009 | Freeman | 606/181 |
| 2009/0139300 A1 | 6/2009 | Pugh | 73/1.36 |
| 2009/0184004 A1 | 7/2009 | Chatelier | 205/777.5 |
| 2009/0187351 A1 | 7/2009 | Orr | 702/19 |
| 2009/0192410 A1 | 7/2009 | Freeman | 600/583 |
| 2009/0192411 A1 | 7/2009 | Freeman | 600/583 |
| 2009/0196580 A1 | 8/2009 | Freeman | 386/124 |
| 2009/0204025 A1 | 8/2009 | Marsot | 600/573 |
| 2009/0216100 A1 | 8/2009 | Ebner | 600/347 |
| 2009/0237262 A1 | 9/2009 | Smith | 340/634 |
| 2009/0240127 A1 | 9/2009 | Ray | 600/365 |
| 2009/0247838 A1 | 10/2009 | Cummings | 600/309 |
| 2009/0247982 A1 | 10/2009 | Krulevitch | 604/500 |
| 2009/0259146 A1 | 10/2009 | Freeman | 600/583 |
| 2009/0280551 A1 | 11/2009 | Cardosi | 435/190 |
| 2009/0281457 A1 | 11/2009 | Faulkner | 600/583 |

| | | | | | | |
|---|---|---|---|---|---|---|
| 2009/0281458 A1 | 11/2009 | Faulkner | 600/583 | EP | 0964060 | 12/1999 |
| 2009/0281459 A1 | 11/2009 | Faulkner | 600/583 | EP | 0969097 | 1/2000 |
| 2009/0301899 A1 | 12/2009 | Hodges | 205/777.5 | EP | 0 985 376 | 5/2000 |
| 2009/0302872 A1 | 12/2009 | Haggett | 324/715 | EP | 1021950 | 7/2000 |
| 2009/0302873 A1 | 12/2009 | Haggett | 324/724 | EP | 0894869 | 2/2001 |
| 2009/0322630 A1 | 12/2009 | Friman | 343/720 | EP | 1074832 | 2/2001 |
| 2009/0325150 A1 | 12/2009 | Haggett | 436/150 | EP | 1093854 | 4/2001 |
| 2010/0016700 A1 | 1/2010 | Sieh | 600/365 | EP | 1 101 443 | 5/2001 |
| 2010/0018878 A1 | 1/2010 | Davies | 205/782 | EP | 1101443 | 5/2001 |
| 2010/0030110 A1 | 2/2010 | Choi | 600/583 | EP | 1114995 | 7/2001 |
| 2010/0041084 A1 | 2/2010 | Stephens | 435/14 | EP | 0736607 | 8/2001 |
| | | | | EP | 1 157 660 | 11/2001 |

FOREIGN PATENT DOCUMENTS

| | | | | | |
|---|---|---|---|---|---|
| | | | EP | 0874984 | 11/2001 |
| DE | 3538313 A1 | 4/1986 | EP | 1157660 | 11/2001 |
| DE | 4212315 A1 | 10/1993 | EP | 0730037 | 12/2001 |
| DE | 4320347 | 12/1994 | EP | 0636879 | 1/2002 |
| DE | 4344452 | 6/1995 | EP | 01174083 | 1/2002 |
| DE | 4420232 | 12/1995 | EP | 0851224 | 3/2002 |
| DE | 29800611 U | 7/1998 | EP | 0759553 | 5/2002 |
| DE | 19819407 | 11/1999 | EP | 0856586 | 5/2002 |
| DE | 200 09 475 | 9/2000 | EP | 0817809 | 7/2002 |
| DE | 20009475 | 10/2000 | EP | 0872728 | 7/2002 |
| DE | 29824204 | 10/2000 | EP | 0795748 | 8/2002 |
| DE | 10032042 | 1/2002 | EP | 0685737 | 9/2002 |
| DE | 10057832 | 2/2002 | EP | 0958495 | 11/2002 |
| DE | 10057832 C1 | 2/2002 | EP | 0937249 | 12/2002 |
| DE | 10142232 | 3/2003 | EP | 1337182 | 8/2003 |
| DE | 10208575 C1 | 8/2003 | EP | 0880692 | 1/2004 |
| DE | 10245721 | 12/2003 | EP | 01374770 | 1/2004 |
| DE | 10361560 A1 | 7/2005 | EP | 1404232 | 4/2004 |
| EP | 0112498 A2 | 7/1984 | EP | 1404233 | 4/2004 |
| EP | 137975 A2 | 4/1985 | EP | 1246688 | 5/2004 |
| EP | 0160768 | 11/1985 | EP | 1502614 | 2/2005 |
| EP | 0199484 A2 | 10/1986 | EP | 1643908 | 4/2006 |
| EP | 0254246 | 1/1988 | EP | 1790288 | 5/2007 |
| EP | 0289 269 | 11/1988 | EP | 1790288 A1 | 5/2007 |
| EP | 0317847 A1 | 5/1989 | EP | 1921992 | 5/2008 |
| EP | 0320109 | 6/1989 | EP | 2039294 | 3/2009 |
| EP | 0 364 208 A1 | 4/1990 | EP | 2039294 A1 | 3/2009 |
| EP | 0170375 | 5/1990 | FR | 2 555 432 A | 5/1985 |
| EP | 0136362 | 12/1990 | FR | 2622457 | 11/1987 |
| EP | 0449525 | 10/1991 | GB | 1558111 | 12/1979 |
| EP | 0453283 | 10/1991 | GB | 2168815 | 6/1986 |
| EP | 0263948 | 2/1992 | GB | 233936 A | 6/1999 |
| EP | 0449147 A2 | 8/1992 | JP | HEI 4 194660 | 7/1992 |
| EP | 0530994 | 3/1993 | JP | 1996010208 | 12/1992 |
| EP | 0374355 | 6/1993 | JP | 1014906 | 1/1998 |
| EP | 0351891 | 9/1993 | JP | 2000-116768 | 4/2000 |
| EP | 0593096 | 4/1994 | WO | WO 80/01389 | 7/1980 |
| EP | 0630609 A2 | 12/1994 | WO | WO 85/04089 | 9/1985 |
| EP | 0415388 | 5/1995 | WO | WO86/05966 | 10/1986 |
| EP | 0654659 | 5/1995 | WO | WO 86/07632 | 12/1986 |
| EP | 0505494 | 7/1995 | WO | WO 91/09139 | 6/1991 |
| EP | 0662367 A1 | 7/1995 | WO | WO92/03099 | 3/1992 |
| EP | 0359831 | 8/1995 | WO | WO92/06971 | 4/1992 |
| EP | 0471986 | 10/1995 | WO | WO92/07263 | 4/1992 |
| EP | 0368474 | 12/1995 | WO | WO92/07468 | 5/1992 |
| EP | 0461601 | 12/1995 | WO | WO93/00044 | 1/1993 |
| EP | 0429076 | 1/1996 | WO | WO 93/06979 | 4/1993 |
| EP | 0552223 | 7/1996 | WO | WO93/09723 | 5/1993 |
| EP | 0735363 | 10/1996 | WO | WO 93/25898 | 12/1993 |
| EP | 0505504 | 3/1997 | WO | WO 94/27140 | 11/1994 |
| EP | 0777123 | 6/1997 | WO | WO 94/29703 | 12/1994 |
| EP | 0406304 | 8/1997 | WO | WO 94/29704 | 12/1994 |
| EP | 0537761 | 8/1997 | WO | WO 94/29731 | 12/1994 |
| EP | 0795601 | 9/1997 | WO | WO 95/00662 | 1/1995 |
| EP | 0562370 | 11/1997 | WO | WO 95/06240 | 3/1995 |
| EP | 0415393 | 12/1997 | WO | WO 95/10223 | 4/1995 |
| EP | 0823239 | 2/1998 | WO | WO95/12583 | 5/1995 |
| EP | 0560336 | 5/1998 | WO | WO 95/22597 | 8/1995 |
| EP | 0878 708 | 11/1998 | WO | WO96/14799 | 5/1996 |
| EP | 0 898 936 A2 | 3/1999 | WO | WO 96/30431 | 10/1996 |
| EP | 0505475 | 3/1999 | WO | WO96/37148 | 11/1996 |
| EP | 0901018 | 3/1999 | WO | WO 97/02359 | 1/1997 |
| EP | 0470649 | 6/1999 | WO | WO 97/02487 | 1/1997 |
| EP | 0 951 939 | 10/1999 | WO | WO 97/11883 | 4/1997 |
| EP | 0 951 939 A2 | 10/1999 | WO | WO 97/11883 A1 | 4/1997 |
| EP | 0847447 | 11/1999 | WO | WO 97/18464 | 5/1997 |
| EP | 0964059 | 12/1999 | WO | WO97/28741 | 8/1997 |

| | | | | | | |
|---|---|---|---|---|---|---|
| WO | WO 97/30344 | 8/1997 | | WO | WO 02/02796 | 1/2002 |
| WO | WO 97/42882 | 11/1997 | | WO | WO 02/08750 | 1/2002 |
| WO | WO 97/42888 | 11/1997 | | WO | WO 02/08753 | 1/2002 |
| WO | WO 97/45720 | 12/1997 | | WO | WO 02/08950 | 1/2002 |
| WO | WO 98/03431 | 1/1998 | | WO | WO 02/18940 | 3/2002 |
| WO | WO98/14436 | 4/1998 | | WO | WO 02/21317 | 3/2002 |
| WO | WO 98/19159 | 5/1998 | | WO | WO 02/25551 | 3/2002 |
| WO | WO98/19609 | 5/1998 | | WO | WO 02/32559 | 4/2002 |
| WO | WO 98/20332 | 5/1998 | | WO | WO 02/41227 | 5/2002 |
| WO | WO 98/20348 | 5/1998 | | WO | WO 02/41779 | 5/2002 |
| WO | WO98/20867 | 5/1998 | | WO | WO 02/44948 | 6/2002 |
| WO | WO 98/24366 | 6/1998 | | WO | WO 02/49507 | 6/2002 |
| WO | WO 98/35225 | 8/1998 | | WO | WO/0249507 | 6/2002 |
| WO | WO98/45276 | 10/1998 | | WO | WO 02/056769 | 7/2002 |
| WO | WO 99/03584 | 1/1999 | | WO | WO 02/059734 | 8/2002 |
| WO | WO 99/05966 | 2/1999 | | WO | WO 02/069791 | 9/2002 |
| WO | WO99/07295 | 2/1999 | | WO | WO 02/077638 | 10/2002 |
| WO | WO 99/07431 A1 | 2/1999 | | WO | WO 02/100251 | 12/2002 |
| WO | WO 99/13100 | 3/1999 | | WO | WO 02/100252 | 12/2002 |
| WO | WO 99/17854 | 4/1999 | | WO | WO 02/100253 | 12/2002 |
| WO | WO 99/18532 | 4/1999 | | WO | WO 02/100254 | 12/2002 |
| WO | WO 99/19507 | 4/1999 | | WO | WO 02/100460 | 12/2002 |
| WO | WO 99/19717 | 4/1999 | | WO | WO 02/100461 | 12/2002 |
| WO | WO 99/27483 | 6/1999 | | WO | WO 02/101343 | 12/2002 |
| WO | WO 99/27852 | 6/1999 | | WO | WO 02/101359 | 12/2002 |
| WO | WO 99/62576 | 12/1999 | | WO | WO 03/000321 | 1/2003 |
| WO | WO 99/64580 | 12/1999 | | WO | WO 03/023389 | 3/2003 |
| WO | WO 00/06024 | 2/2000 | | WO | WO 03/042691 | 5/2003 |
| WO | WO 00/09184 | 2/2000 | | WO | WO 03039369 A | 5/2003 |
| WO | WO 00/11578 | 3/2000 | | WO | WO 03/045557 | 6/2003 |
| WO | WO 00/15103 | 3/2000 | | WO | WO 03/046542 | 6/2003 |
| WO | WO 00/17799 | 3/2000 | | WO | WO 03/049609 | 6/2003 |
| WO | WO 00/17800 | 3/2000 | | WO | WO 03/050534 | 6/2003 |
| WO | WO 00/18293 | 4/2000 | | WO | WO 03/066128 | 8/2003 |
| WO | WO 00/19346 | 4/2000 | | WO | WO 03/070099 | 8/2003 |
| WO | WO 00/20626 | 4/2000 | | WO | WO 03/071940 | 9/2003 |
| WO | WO00/29577 | 5/2000 | | WO | WO 03/082091 | 10/2003 |
| WO | WO 00/30186 | 5/2000 | | WO | WO 03/082091 A2 | 10/2003 |
| WO | WO 00/32097 | 6/2000 | | WO | WO 03/088824 | 10/2003 |
| WO | WO 00/32098 | 6/2000 | | WO | WO 03/088834 | 10/2003 |
| WO | WO 00/33236 | 6/2000 | | WO | WO 03/088835 | 10/2003 |
| WO | WO 00/39914 | 7/2000 | | WO | WO/03088834 | 10/2003 |
| WO | WO 00/42422 | 7/2000 | | WO | WO 03/094752 | 11/2003 |
| WO | WO 00/44084 | 7/2000 | | WO | WO 03/101297 | 12/2003 |
| WO | WO00/46854 | 8/2000 | | WO | WO 2004/008130 | 1/2004 |
| WO | WO 00/50771 | 8/2000 | | WO | WO 2004/022133 | 3/2004 |
| WO | WO00/55915 | 9/2000 | | WO | WO 2004/026130 | 4/2004 |
| WO | WO 00/60340 | 10/2000 | | WO | WO 2004/040285 A2 | 5/2004 |
| WO | WO 00/64022 | 10/2000 | | WO | WO 2004/040287 A1 | 5/2004 |
| WO | WO 00/67245 | 11/2000 | | WO | WO 2004/040948 | 5/2004 |
| WO | WO 00/67268 | 11/2000 | | WO | WO 2004/041082 | 5/2004 |
| WO | WO 00/72452 | 11/2000 | | WO | WO 2004/045375 | 6/2004 |
| WO | WO 01/00090 | 1/2001 | | WO | WO 2004/054455 | 7/2004 |
| WO | WO 01/15807 | 3/2001 | | WO | WO 2004/060174 | 7/2004 |
| WO | WO 01/16578 A1 | 3/2001 | | WO | WO 2004/060446 | 7/2004 |
| WO | WO 01/75433 | 3/2001 | | WO | WO 2004/091693 | 10/2004 |
| WO | WO 01/23885 | 4/2001 | | WO | WO 2004/098405 | 11/2004 |
| WO | WO 01/25775 | 4/2001 | | WO | WO 2004/003147 | 12/2004 |
| WO | WO 01/26813 | 4/2001 | | WO | WO 2004/107964 | 12/2004 |
| WO | WO01/29037 | 4/2001 | | WO | WO 2004/107975 | 12/2004 |
| WO | WO 01/33216 | 5/2001 | | WO | WO 2004/112602 | 12/2004 |
| WO | WO 01/34029 | 5/2001 | | WO | WO 2004/112612 | 12/2004 |
| WO | WO 01/36955 | 5/2001 | | WO | WO 2004/112612 A1 | 12/2004 |
| WO | WO 01/37174 | 5/2001 | | WO | WO 2005/001418 | 1/2005 |
| WO | WO 01/45014 A1 | 6/2001 | | WO | WO 2005/006939 | 1/2005 |
| WO | WO 01/40788 | 7/2001 | | WO | WO 2005/011774 | 2/2005 |
| WO | WO 01/57510 | 8/2001 | | WO | WO 2005/013824 | 2/2005 |
| WO | WO 01/63271 | 8/2001 | | WO | WO 2005/016125 | 2/2005 |
| WO | WO 01/64105 | 9/2001 | | WO | WO 2005/018425 | 3/2005 |
| WO | WO 01/66010 | 9/2001 | | WO | WO 2005/018430 | 3/2005 |
| WO | WO 01/69505 | 9/2001 | | WO | WO 2005/018454 | 3/2005 |
| WO | WO 01/72220 A | 10/2001 | | WO | WO 2005/018709 | 3/2005 |
| WO | WO 01/72225 | 10/2001 | | WO | WO 2005/018710 | 3/2005 |
| WO | WO 01/73124 | 10/2001 | | WO | WO 2005/018711 | 3/2005 |
| WO | WO 01/73395 | 10/2001 | | WO | WO 2005/022143 | 3/2005 |
| WO | WO 01/89691 | 11/2001 | | WO | WO 2005/023088 | 3/2005 |
| WO | WO01/95806 | 12/2001 | | WO | WO 2005/033659 | 4/2005 |
| WO | WO 01/95806 | 12/2001 | | WO | WO 2005/034720 | 4/2005 |
| WO | WO 02/00101 | 1/2002 | | WO | WO 2005/034721 | 4/2005 |

| | | | | | | |
|---|---|---|---|---|---|---|
| WO | WO 2005/034741 | 4/2005 | | WO | WO 2005/121759 | 12/2005 |
| WO | WO 2005/034778 | 4/2005 | | WO | WO 2006/001797 | 1/2006 |
| WO | WO 2005/035017 | 4/2005 | | WO | WO 2006/001973 | 1/2006 |
| WO | WO 2005/035018 | 4/2005 | | WO | WO 2006/011062 | 2/2006 |
| WO | WO 2005/037095 | 4/2005 | | WO | WO 2006/013045 | 2/2006 |
| WO | WO 2005/046477 | 5/2005 | | WO | WO 2006/015615 | 2/2006 |
| WO | WO 2005/065399 | 7/2005 | | WO | WO 2006/027702 A2 | 3/2006 |
| WO | WO 2005/065414 | 7/2005 | | WO | WO 2006/031920 | 3/2006 |
| WO | WO 2005/065415 | 7/2005 | | WO | WO 2006/032391 | 3/2006 |
| WO | WO 2005/065545 | 7/2005 | | WO | WO 2006/072004 | 7/2006 |
| WO | WO 2005/072604 | 8/2005 | | WO | WO 2006/105146 | 10/2006 |
| WO | WO2005/084546 A2 | 9/2005 | | WO | WO 2006/116441 | 11/2006 |
| WO | WO 2005/084557 | 9/2005 | | WO | WO 2007/025635 | 3/2007 |
| WO | WO 2005/104948 | 11/2005 | | WO | WO 2007/044834 | 4/2007 |
| WO | WO 2005/104948 A1 | 11/2005 | | WO | WO 2007/054335 | 5/2007 |
| WO | WO 2005/114185 | 12/2005 | | WO | WO 2007/070719 | 6/2007 |
| WO | WO 2005/116622 | 12/2005 | | WO | WO 2007/084367 | 7/2007 |
| WO | WO 2005/119234 | 12/2005 | | WO | WO 2007/106470 | 9/2007 |
| WO | WO 2005/120197 | 12/2005 | | WO | WO 2007/119900 | 10/2007 |
| WO | WO 2005/120199 | 12/2005 | | WO | WO 2008/112268 | 9/2008 |
| WO | WO 2005/120365 | 12/2005 | | WO | WO 2008/112279 | 9/2008 |
| WO | WO 2005/120365 A1 | 12/2005 | | | | |

* cited by examiner

DEVICE AND METHOD FOR VARIABLE SPEED LANCET

RELATED APPLICATIONS

This application is a divisional of U.S. Ser. No. 10/420,535, filed Apr. 21, 2003 now U.S. Pat. No. 7,258,693, which is a continuation in part of commonly assigned, U.S. patent application Ser. No. 10/324,053 filed Dec. 18, 2002 now U.S. Pat. No. 7,713,214, which is a continuation-in-part of U.S. patent application Ser. No. 10/127,395, filed on Apr. 19, 2002, now U.S. Pat. No. 7,025,774. Said 10/324,053 claims the benefit of priority to U.S. Provisional Patent Application Ser. No. 60/374,304 filed Apr. 19, 2002 and copending U.S. patent application Ser. No. 10/127,201 filed on Apr. 19, 2002. The present application is also related to U.S. patent application Ser. Nos. 10/335,182, 10/335,142, 10/335,215, 10/335,258, 10/335,099, 10/335,219, 10/335,052, 10/335,073, 10/335,220, 10/335,252, 10/335,218, 10/335,211, 10/335,257, 10/335,217, 10/335,212, 0/335,241, 10/335,183, 10/335,082, 10/335,240, 10/335,259, filed Dec. 31, 2002. Said 10/324,053 is also related to PCT Application PCT/US03/12555 filed on Apr. 21, 2003. All applications listed above are incorporated herein by reference in their entirety for all purposes.

BACKGROUND

Lancing devices are known in the medical health-care products industry for piercing the skin to produce blood for analysis. Typically, a drop of blood for analysis is obtained by launching or driving a lancet into tissue to create a small incision, which generates a small blood droplet on the tissue surface.

Current mechanical lancet launchers are configured to actuate ballistically. The lancet is driven out from the opening in the launcher and when a predetermined penetration depth is reached, a return spring propels the lancet back into the housing depth is reached, a return spring propels the lancet back into the housing with roughly the same velocity as for the inbound. There is no mechanism to control the lancet in flight (inbound or outbound) other than a hard stop for maximum penetration. It is therefore impossible to control lancet velocity for skin properties, let alone skin anatomy differences, in these devices other than a crude depth setting. Known launchers may use stepped offsets in a range of 0.9 mm to 2.3 mm or switchable end caps to attempt to control lancet depth. The thicker the offset, the shallower the resulting penetration. These depth settings are, in actuality, a measurement of the protrusion of the lancet tip from the housing, and do not reflect the actual penetration depth of the lancet because of tenting or bending of skin before or during cutting. Unfortunately, without reliable lancet control during actuation, the pain and other drawbacks associated with using known mechanical lancet launchers discourage patients from following a structured glucose monitoring regime.

SUMMARY OF THE INVENTION

The present invention provides solutions for at least some of the drawbacks discussed above. Specifically, some embodiments of the present invention provide improved control of lancet or penetrating member velocity. At least some of these and other objectives described herein will be met by embodiments of the present invention. In one aspect of the present invention, a method of penetrating tissue is provided. The method comprises using a lancet driver to advance a lancet into the tissue; advancing the lancet at a first desired velocity in a first layer of tissue; advancing the lancet at a second desired velocity in a second layer of tissue; and advancing the lancet at a third desired velocity in a third layer of tissue. In one embodiment, the method may including using a processor having logic for controlling velocity of the lancet in each layer of tissue. In another embodiment, the first velocity is at least partially determined based on hydration of the stratum corneum. It should also be understood that the lancet driver may be electromechanical. The velocity may be determined based on cell population and distribution in the different zones of tissue. The processor may also determine what proportion of electrical power consumption is related to the stratum corneum by measuring differences between normal and hydrated stratum corneum. In another embodiment according to the present invention, a method is provided for penetrating tissue. The method comprises using a drive force generator to advance a penetrating member along a penetration path into the tissue wherein the penetrating member having a penetrating member velocity equal to a first velocity in a first layer of tissue. Penetrating member velocity is determined at a plurality of locations along the penetration path. The method also includes adjusting penetrating member velocity at a plurality of locations along the penetration path prior to the penetrating member coming to a stop in the tissue. In another embodiment, the method may further include advancing the penetrating member at a maximum velocity through the stratum corneum, at a velocity in the epidermis sufficient to reduce shock waves to pain sensor in dermis, and at a velocity in the dermis is sufficient for efficient cutting of blood vessels without stimulating pain sensors.

In another aspect of the present invention, a lancing system is provided to drive a lancet during a lancing cycle and for use on a tissue site. The system comprises a lancet driver; a processor coupled to said lancet driver, the processor configured to adjust lancet velocity to achieve a desired velocity based on the layer of tissue through which the lancet is cutting. The system may include a user interface allowing a user to adjust penetration depth based on stratum corneum hydration. The user interface may also allow a user to adjust lancet velocity based on user pain. The system may also include memory for storing at least one of the following to determine a skin profile: energy consumed per lancing event; time of day of. In a still further aspect of the present invention, a further method of driving a lancet into a tissue site is provided. The method comprises calculating stratum corneum thickness based on energy consumed and depth of lancet penetration on a previous lancing cycle; driving the lancet into the tissue site, wherein the lancet does not penetrate more than a desired distance beyond the stratum corneum thickness, the stratum corneum thickness determined by an inflection point of energy consumption when the lancet exits that layer. A further understanding of the nature and advantages of the invention will become apparent by reference to the remaining portions of the specification and drawings.

DESCRIPTION

Figure 1:
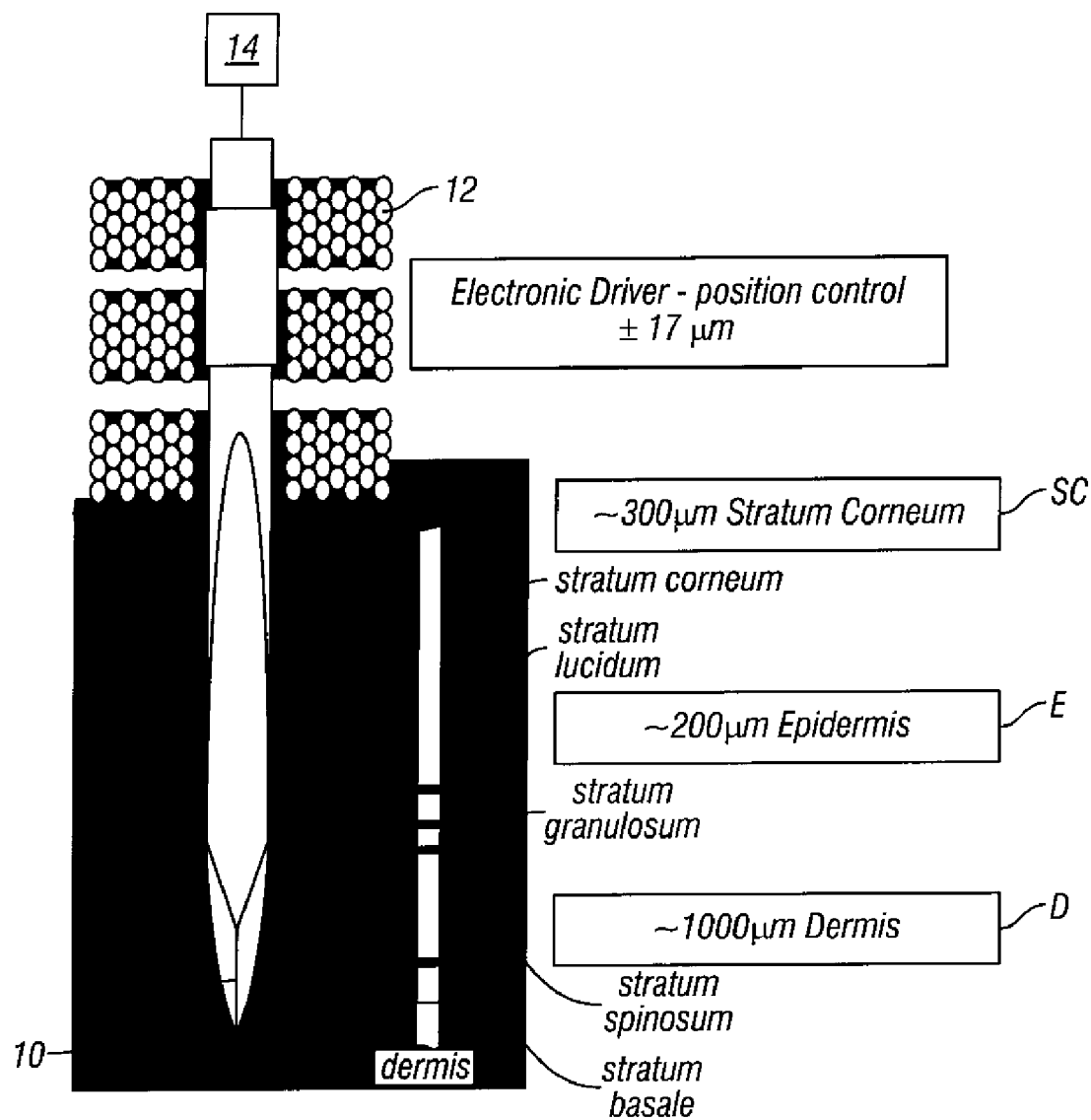
FIG. 1 is a diagram shows a lancet penetrating layers of the skin in a histological section.

It is to be understood that both the foregoing general description and the following detailed description are exemplary and explanatory only and are not restrictive of the invention, as claimed. It should be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

The pain and sufficiency of blood yield of a capillary blood sample from the skin may vary based in part on the efficiency of the cutting device within skin layers. Specifically, the ability to control the lancet trajectory in terms of the velocity profile within the spatial constraints of the skin layers will determine, at least in part, how painless, and how efficient the cutting is.

There is a regional variation in cell type from the surface of the skin down through the epidermis and dermis. As a non-limiting example, cutting the blood vessels yields blood volumes of about 1-3 μL using lancets of diameters 300 to 400 pm at depths of about 0.1-1.5 mm. It is desirable, in one embodiment, to only penetrate deep enough to reach and cut the required amount of blood vessels for a blood sample. Penetrating too deep causes more pain than necessary, penetrating too shallow does not yield enough blood or no blood. In one embodiment, cutting the capillaries in the superficial reticular layer of the dermis with a 300 pm diameter lancet is sufficient to yield enough blood to fill current state of the art glucose test strips using 0.3-0.5 μL of blood.

In one ideal situation, a painless incision by the lancet would cut enough blood vessels to yield a spontaneous blood sample, which would reach the surface of the tissue for analyte testing for such metabolites as glucose without cutting many nerves or disturbing the elastin fiber net, collagen fibers. Efficient cutting would be defined as controlled lancing for minimal pain to yield a required blood volume for testing at a shallow depth which equates to cutting the capillary mesh in the superficial reticular layer.

Using an electronically driven lancet, (where position and velocity are accurately controlled) the user can fine-tune the cutting process depending on the cell population and distribution in the different layers, for example, based on whether nerves are present or not, or based on the elastin or collagen fiber content orientation or distribution.

Accurate depth control relates to generating a spontaneous blood sample with minimum pain. It is desirable, in one embodiment, to vary the velocity of the cutting lancet based on the cell population. The surface of the skin is comprised of dead or dying cells (the stratum corneum). It is a horny layer, which may vary from 100 μm to 600 μm in thickness, and represents the top layer of the epidermis. The deeper layers of the epidermis can be grouped into 5 different layers, the last of which separates it from the dermis. The epidermis has little innervation compared to the dermis. The distance from the bottom of the stratum corneum to the capillary loops of the dermal papillae is about 300 μm. In one embodiment, using an electric lancet actuator coupled with a position transducer, it is possible to resolve position of the lancet within the skin to an accuracy of ±17 μm. This translates in to over 40 steps through which the velocity can be fed back and controlled. It should be understood, of course, that sensors of other accuracies, as known in the art, may also be used. Embodiments of the invention include devices and methods to control the velocity of the lancet within the different anatomical layers of the skin to achieve the most efficient cutting. Advantages are achieved by use of a miniaturized electronic lancing system for efficiently cutting through the layers of skin by optimizing the velocity profile and using position control feedback mechanism is described.

Referring now to FIG. 1, layers of the skin are shown in this histological section. Skin is composed of various distinct anatomical regions (FIG. 1). The main function of the epidermis E is to protect the body from harmful influences from the environment and against fluid loss. The dermis D is the thick layer of connective tissue to which the epidermis D is attached.

The epidermis E is composed of an outermost layer is the stratum corneum, which mainly consists of dead keratinized cells. Variations in the thickness of the epidermis (−0.1 mm. in thin skin, 1 mm or more in thick skin) are mainly the result of variations in the thickness of the stratum corneum (SC). The epidermis E composed of stratum lucidum (consisting of several layers of flattened dead 30 cells), stratum granulosum (consisting of a few layers of flattened cells) stratum spinosum (cells are irregularly polygonal and often separated by narrow, translucent clefts), and stratum basale. Stratum basale is the deepest layer or zone of the epidermis and separates the epidermis from the dermis. It consists of a single layer of columnar or cuboidal cells, which rest on the basement membrane. Basal cells are the stem cells of the epidermis.

The dermis D is where capillaries and blood vessels are located and nerves supported by connective tissue including collagen fibers and elastin are found. The collagen fibers give the dermis its strength, the elastin and microfibrils give skin its elasticity. Its deepest part continues into the subcutaneous tissue without a sharply defined boundary making thickness difficult to determine. It is about 1-2 mm for "average" skin.

For a blood sample to reach the surface of the tissue or skin following lancing, several factors come in to play. The lancet may cut through each layer, it may reach the required depth to cut a sufficient number of blood vessels for the desired blood volume, and then the blood may be able to flow up the wound tract created by the lancet and arrive at the surface of the skin. If blood arrives at the surface of the finger without "milking" of the finger, this is called a 'spontaneous' blood sample. Generating a spontaneous blood sample is crucial when interfacing a measurement unit (e.g. test strip) to the lancing event. The lancet penetration may be deep enough that adequate vessels are cut to release the blood, and not too deep that unnecessary pain is generated. Thus accurate depth control is the primary factor controlling a spontaneous blood sample.

Maintaining wound patency is also a factor for achieving a "successful" bleeding event. Many times blood is prevented from flowing upstream the wound channel due to closure of the channel by retraction forces of surrounding elastic fibers, which cause the wound channel to close before the blood can surface.

Keeping the wound open and allowing spontaneous blood flow can be achieved by slowly retracting the lancet up the wound channel.

As seen in FIG. 1, the thickness of the stratum corneum SC, epidermis E and dermis D are given for comparison. In one embodiment, the lancet or penetrating member 10 driven along a penetration path by an electronic driver 12, may reach the blood vessels located in the dermis D, and cut enough of them to produce a sample of blood for testing. In one embodiment, the cutting process may be as painless as possible. This may be achieved by a rapid cutting speed and accurate control of depth of penetration.

Figure 2:
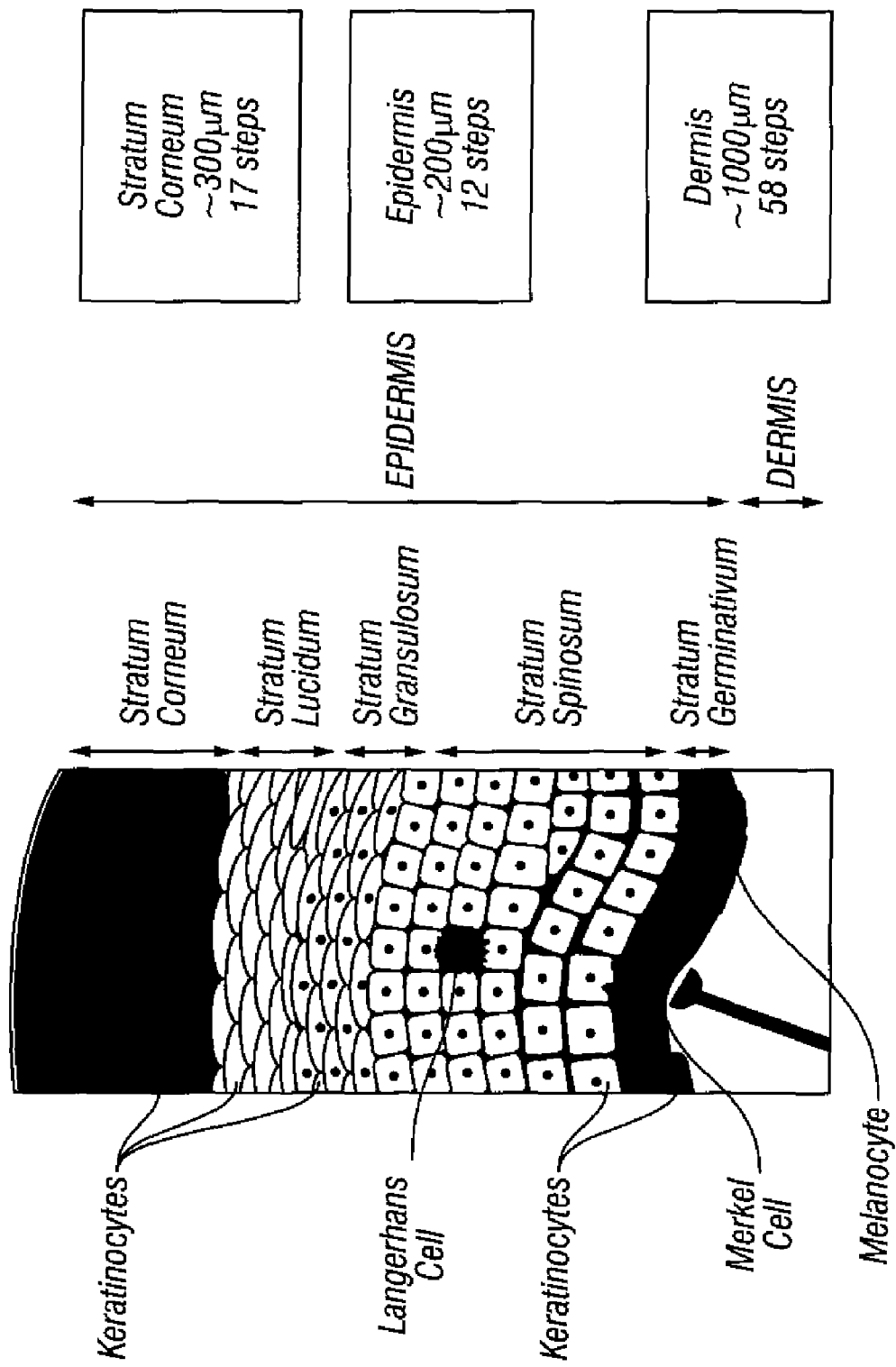
FIG. 2 is a skin anatomy drawing showing the various skin layers with distinct cell types.

The ability to control the lancet or penetrating member trajectory in terms of the velocity profile of the lancet or penetrating member 10 within the spatial constraints of the skin layers may result in less painful, more efficient cutting of the skin. In one embodiment, the user can fine tune the cutting process depending on the skin layer and cell population of the different zones using an electronically driven lancet 10, where position and velocity are accurately controlled i.e. whether nerves are present or not as seen in FIG. 2. Specifically, FIG. 2 shows skin anatomy relevant to capillary blood sampling. The skin layers are comprised of distinct cell types. Variation of lancet velocity based on cell populations in the different layers allows for very precise cutting.

For an electronic or electromechanical lancet driver 12, such as the controllable electronic drivers described in copending U.S. patent application titled "Tissue Penetration Device" (Attorney Docket No. 38187-2551), operating at a lancing velocity in the range of about 4-10 m/s is possible. This is two to four times faster than the commonly available mechanically actuated devices, (which operate in the range of 1-2 m/s). Ballistic mechanical launcher devices are also not equipped with position feedback mechanisms. Depth control in these devices is usually by an end cap with stepped offsets. The lancet barrel hitting the back of the cap controls the lancet depth. The thicker the offset, the shallower the resulting penetration. Users select the depth they prefer by dialing in the number represented on the device. In one embodiment, penetration settings vary from about 0.5-2.0 mm with steps of about 0.2 mm to 0.4 mm. The accuracy of the depth variation is of the order of ±0.1 mm with the selected puncture depth.

As a nonlimiting example, using an electric lancet driver 12 coupled to an optical position sensor 14, velocity of the lancet 10 may be controlled at any stage during the actuation and retraction. In one embodiment, the accuracy of the device in terms of position may be different for the inbound and outbound phase of the movement. Two different types of sensor readings may be applied for the inbound and the outbound. The current embodiment achieves 70 μm accuracy on the inbound phase using a so called "single (falling) edge detection" and 17 μm for the outbound, using a so called "four (rising and falling) edge detection". In this nonlimiting example, the accuracy of the velocity control is within 1% at a speed of 5 m/s.

Figure 3:
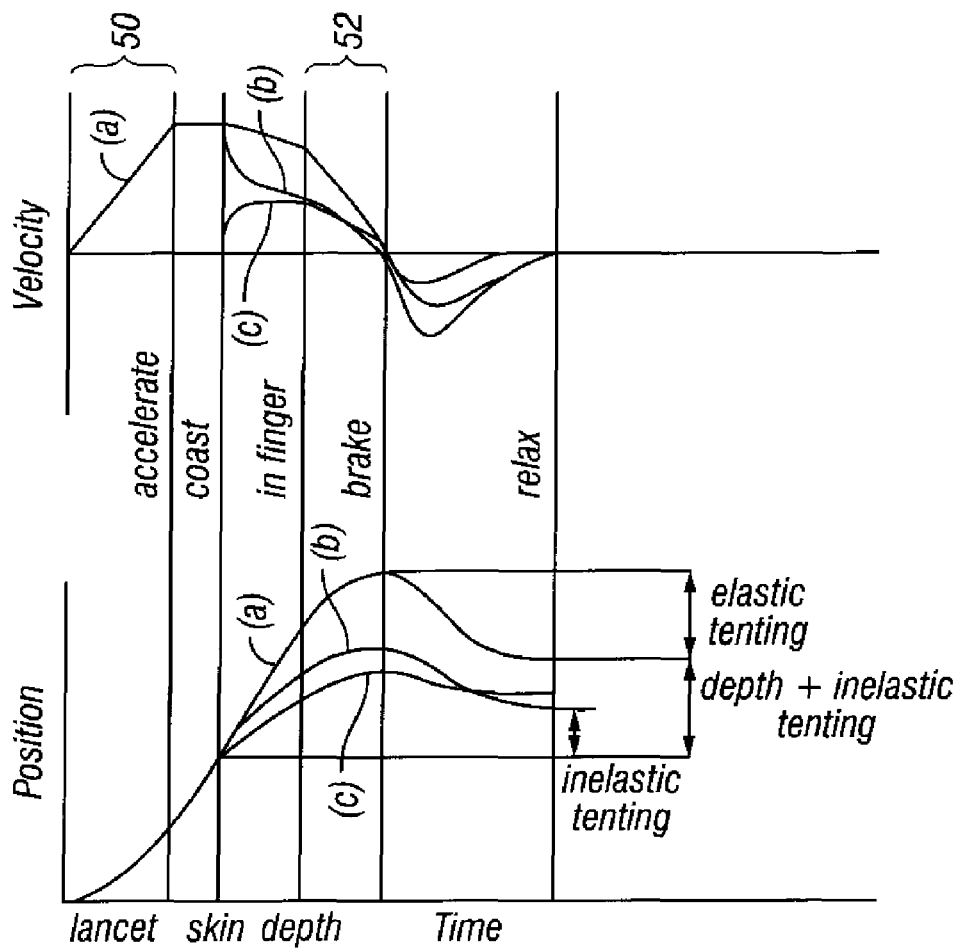
FIG. 3 shows lancet trajectories plotted in terms of velocity and position. Line (a) indicates the lancet position, line (b) indicates the skin position as it interacts with the lancet. Line (c) indicates the actual penetration depth of the lancet within the skin.

Referring now to FIG. 3 for another nonlimiting example, lancet position and velocity during an actuation and retraction event is shown. Lancet trajectories in FIG. 3 are plotted in terms of velocity and position. Line (a) indicates the lancet position, line (b) indicates the skin position as it interacts with the lancet. Line (c) indicates the actual penetration depth of the lancet within the skin. The difference between the elastic tenting or bending of the skin and the lancet position is the actual depth of penetration. Skin tenting can account for up to 100 μm. Inelastic tenting (the fact that the skin does not return to it original position post lancet removal) is on average about 100 μm. The invention focuses on controlling the lancet velocity while on the inbound trajectory in the finger skin.

As seen in FIG. 3, the lancet 10 in one embodiment undergoes an acceleration phase 50 to a specified velocity from where it coasts until it contacts the skin. This velocity may be preset. At this point any type of velocity profile can be defined until it reaches the target depth. There is a braking period 52 included which allows the lancet 10 to come to a complete stop at the selected 20 penetration depth for this embodiment. The lancet 10 is then retracted from the tissue or finger, and returns to the housing.

Figure 4:
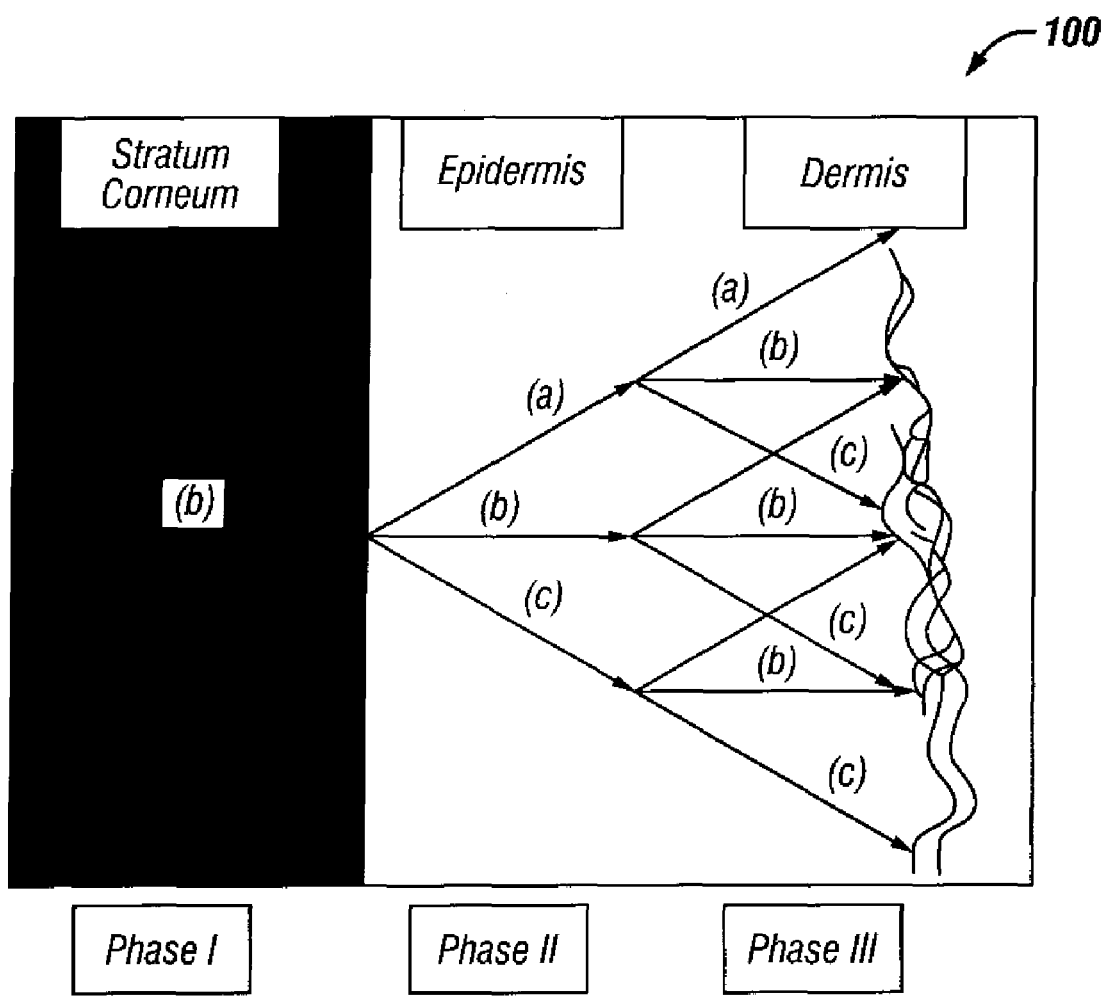
FIG. 4 is a diagram showing variation of lancet velocity through different phases of the inbound trajectory.

Referring now to FIG. 4, the area of interest is the velocity profile 100 while the lancet is cutting through the skin layers in the finger until it reaches a predetermined depth. More specifically, variation of lancet velocity through different phases of the inbound trajectory is shown in FIG. 4. In this embodiment, Phase I corresponds to the stratum corneum, phase II to the epidermis and phase III to the dermis. At each phase (and during the phase), the options are to maintain current velocity, increase current velocity or decrease current velocity. Based on the thickness of the stratum corneum, velocity could be monitored and changed in this embodiment at 9 points in the stratum corneum, 6 points in the epidermis, and 29 points in the dermis using the four edge detection algorithm and the 360 strips per inch encoder strip. It should be noted that although the embodiment of the driver discussed herein produces the previously discussed number of monitoring points for a given displacement, other driver and position sensor embodiments may be used that would give higher or lower resolution.

For the purposes of the present discussion for this nonlimiting example, the skin is viewed as having three distinct regions or tissue layers: the stratum corneum SC (Phase I), the epidermis E (Phase II) and the dermis D (Phase III). In one embodiment, the lancet 10 is accelerated to a first desired velocity. This velocity may be predetermined or it may be calculated by the processor during actuation. The processor is also used to control the lancet velocity in tissue. At this velocity, the lancet 10 will impact the skin and initiate cutting through the stratum corneum. The stratum corneum is hard, hence in this embodiment, maximum velocity of the lancet 10 may be employed to efficiently cut through this layer, and this velocity may be maintained constant until the lancet passes through the layer. Power will likely need to be applied to the lancet drive 12 while the lancet is cutting through the stratum corneum in order to maintain the first velocity. Average stratum corneum thickness is about 225 μm. Using a four-edge detection algorithm for the position sensor 14 of this embodiment, the opportunity to verify and feed back velocity information can be carried out at 225/17 or roughly 13 points. In another embodiment accelerating through the stratum corneum following impact may improve cutting efficiency. Acceleration may be possible if the lancet has not reached its target or desired velocity before impact. FIG. 4 shows the result of increasing ((a) arrows, maintaining ((b) arrows) or reducing ((c) arrows) velocity on the lancet trajectory for each of the tissue layers.

On reaching the epidermis E (Phase II), an embodiment of a method may decrease the velocity ((c) arrows) from the first velocity so that tissue compression is reduced in this second tissue layer. Thus the lancet 10, in this nonlimiting example, may have a second desired velocity that is less than the first velocity. The reduced speed in the second tissue layer may reduce the pain experienced by the mechano receptor nerve cells in the dermal layer (third tissue layer). In the absence of tissue compression effects on the dermal layer, however, lancet velocity may be kept constant for efficient cutting (i.e. second velocity may be maintained the same as the first velocity). In another embodiment, velocity may be increased in the second tissue layer from the first velocity.

In Phase III, the lancet or penetrating member 10 may reach the blood vessels and cut them to yield blood. The innervation of this third tissue layer and hence pain perception during lancing could be easily affected by the velocity profile chosen. In one embodiment, a third desired velocity may be chosen. The velocity may be chosen to minimize nerve stimulation while maintaining cutting efficiency. One embodiment would involve reducing velocity from the second velocity to minimize pain, and may increase it just before the blood vessels to be cut. The number of velocity measurement steps possible for the position sensor described above in the dermis is approximately 58. The user would determine the best velocity/cutting profile by usage. The profile with the least amount of pain on lancing, yielding a successful blood sample would be programmable into the device.

Currently users optimize depth settings on mechanical launchers by testing various settings and through usage, settle on a desired setting based on lancing comfort. Embodiments of the device and methods discussed herein provide a variety of velocity profiles (FIG. 4), which can be optimized by the user for controlled lancing, and may include: controlling the cutting speed of a lancet with the lancet within the skin; adjusting the velocity profile of the lancet while the lancet is in the skin based upon the composition of the skin layers; lancing according to precise regional velocity profiles based on variation in cell type from the surface of the skin down through the epidermis and dermis; lancing at a desired velocity through any tissue layer and varying the velocity for each layer. This may include maximum velocity through the stratum corneum, mediation of velocity through epidermis to minimize shock waves to pain sensors in dermis, and mediation of velocity through dermis for efficient cutting of blood vessels without stimulating pain receptors.

Figure 5:
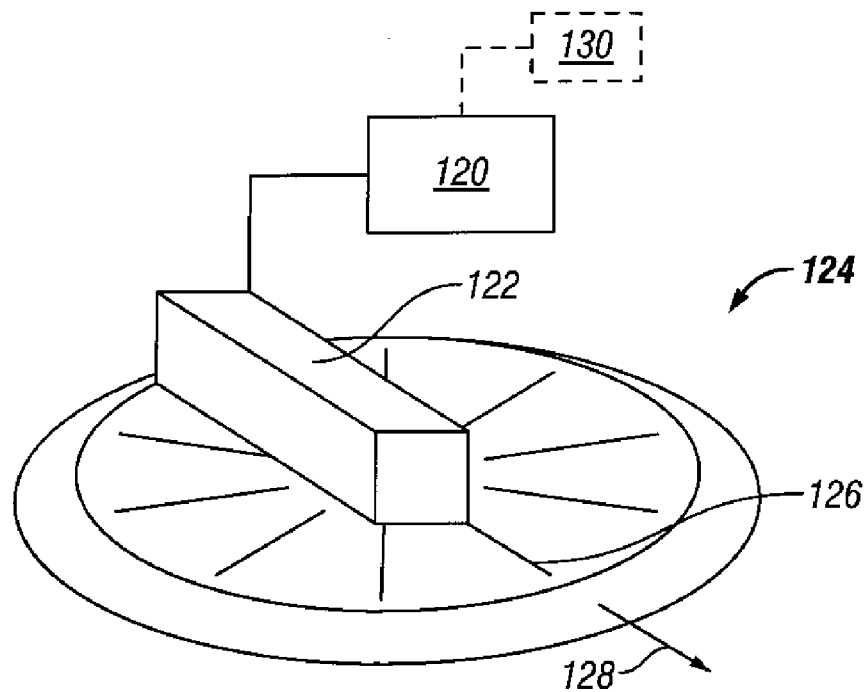
FIG. 5 shows one embodiment of an invention according to the present invention for use with a multiple lancet cartridge.

Referring now to FIG. 5, a processor 120 according to the present invention is used to control the lancet driver 122. As previously discussed, a suitable lancet driver may be found in commonly assigned, U.S. patent application titled "Tissue Penetration Device" now U.S. Pat. No. 7,025,774 filed on Apr. 19, 2002. The lancet or penetrating member driver may be adapted for use with a cartridge 124 holding a plurality of lancets or penetrating members 126 which may be actuated to extend outward as indicated by arrow 128. A suitable cartridge may be found in commonly assigned, copending U.S. patent application Ser. No. 10/324,053, now U.S. Pat. No. 7,713,214 filed on Dec. 18, 2002. The system may also include memory 130 for storing at least one of the following to determine a skin profile: energy consumed per lancing event; stratum corneum hydration; time of day of stratum corneum hydration measurement.

Figure 6:
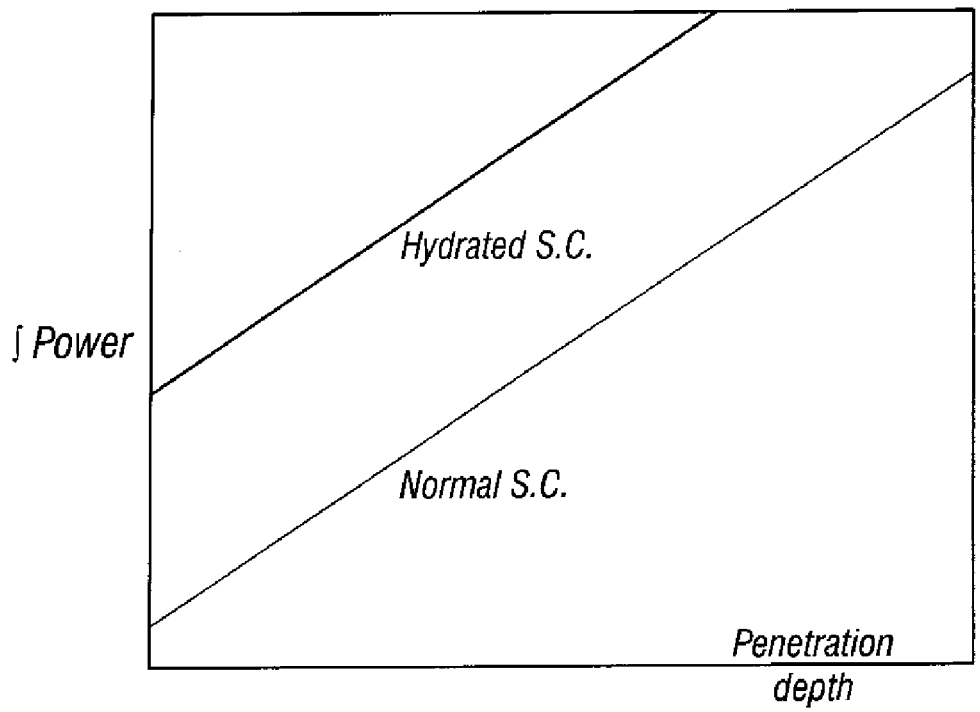
FIG. 6 is a graph showing a difference in power depending on the level of stratum corneum hydration.

Referring now to FIG. 6, the amount of power used to penetrate into the tissue may increase with increased hydration of the stratum corneum. The present invention provides methods for compensating for variation in stratum corneum hydration. Hydration has its strongest effect in the outer layer of the stratum corneum. Studies have shown that coenocytes can swell up to 80% larger on hydration. It is useful to determine what proportion of electrical power consumption is related the change in thickness of stratum corneum from measuring electrical property differences between normal and hydrated stratum corneum. The present invention determines the amount of energy used to achieve a certain penetration depth at various states of stratum corneum hydration. By recording a history of penetration energy and the hydration level, the amount of extra energy used during lancing may be attributed to the change in thickness of the stratum corneum brought about by increased or decreased hydration. In one embodiment, the user will adjust penetration depth, lancing velocity, lancing velocity for certain tissue layers, time of day, or to account for in stratum corneum variations due to hydration level.

The pain and efficiency of blood yield of a capillary blood sample from the skin may very well depend on the efficiency of the cutting device within skin layers. The ability to control the lancet trajectory in terms of the velocity profile within the skin layers will determine how painless, and how efficient the cutting is. Using an electronically driven lancet, where position and velocity are accurately controlled the user can finetune the cutting process depending on the cell population and distribution in the different zones for efficient, painless and reproducible lancing.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. Some other advantages of the disclosed embodiments and features of additional embodiments include: a high number of penetrating members such as 25, 50, 75, 100, 500, or more penetrating members may be put on a disk or cartridge; molded body about a lancet may be used but is not a necessity; manufacturing of multiple penetrating member devices is simplified through the use of cartridges; handling is possible of bare rods metal wires, without any additional structural features, to actuate them into tissue; maintaining extreme (better than 50 micron—lateral—and better than 20 micron vertical) precision in guiding; and storage system for new and used penetrating members, with individual cavities/slots is provided. Any of the dependent claims which follow may be combined with any independent claim which follows.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A lancing system configured to drive a lancet during a lancing cycle and used on a tissue site, the system comprising:
a controllable electronic lancet driver coupled to the lancet;
a position sensor coupled to the controllable electronic lancet driver, the position sensor configured to detect position and velocity of the lancet in the tissue site; and
a processor coupled to said controllable electronic lancet driver, said processor configured to adjust velocity of the lancet to advance the lancet at a first desired velocity in a first layer of tissue, at a second desired velocity in a second layer of tissue, and at a third desired velocity in a third layer of tissue based on feedback of the position and velocity of the lancet from the position sensor.

2. The system of claim 1 further comprising a user interface on said lancet driver allowing a user to adjust penetration depth based on stratum corneum hydration.

3. The system of claim 1 further comprising a user interface on said lancet driver allowing a user to adjust lancet velocity based on user pain.

4. The system of claim 1 further comprising memory for storing at least one of the following to determine a skin profile: energy consumed per lancing event; stratum corneum hydration; time of day of stratum corneum hydration measurement.

5. The system of claim 1 wherein:
said processor has logic for using the lancet driver to advance the lancet into said tissue, said lancet having the lancet velocity equal to the first velocity in the first layer of tissue; adjusting lancet velocity in the skin to achieve the desired velocity based on the layer of tissue through which the lancet is cutting to provide advancement of the lancet at the first desired velocity in the first layer of tissue, at the second desired velocity in the second layer of tissue, and at the third desired velocity in the third layer of tissue.

* * * * *